US010745692B2

(12) United States Patent
Murakami et al.

(10) Patent No.: US 10,745,692 B2
(45) Date of Patent: Aug. 18, 2020

(54) PRODUCTION METHOD FOR CHARGED NON-PROTEIN AMINO ACID-CONTAINING PEPTIDE

(71) Applicants: The University of Tokyo, Tokyo (JP); PeptiDream Inc., Kanagawa (JP)

(72) Inventors: Hiroshi Murakami, Tokyo (JP); Takashi Kawakami, Tokyo (JP); Patrick Reid, Tokyo (JP); Toru Sasaki, Tokyo (JP)

(73) Assignees: The University of Tokyo, Tokyo (JP); PeptiDream Inc., Kanagawa (JP)

( * ) Notice: Subject to any disclaimer, the term of this patent is extended or adjusted under 35 U.S.C. 154(b) by 574 days.

(21) Appl. No.: 14/910,009

(22) PCT Filed: Aug. 4, 2014

(86) PCT No.: PCT/JP2014/070487
§ 371 (c)(1),
(2) Date: Mar. 28, 2016

(87) PCT Pub. No.: WO2015/019999
PCT Pub. Date: Feb. 12, 2015

(65) Prior Publication Data
US 2016/0289668 A1 Oct. 6, 2016

(30) Foreign Application Priority Data

Aug. 5, 2013 (JP) .................................. 2013-162440

(51) Int. Cl.
*C12N 15/10* (2006.01)
*C07K 7/06* (2006.01)
*C12N 15/67* (2006.01)
*C12P 21/02* (2006.01)
*G01N 33/68* (2006.01)
*G01N 33/53* (2006.01)

(52) U.S. Cl.
CPC ............ *C12N 15/1062* (2013.01); *C07K 7/06* (2013.01); *C12N 15/67* (2013.01); *C12P 21/02* (2013.01); *G01N 33/5308* (2013.01); *G01N 33/6845* (2013.01); *Y02P 20/55* (2015.11)

(58) Field of Classification Search
None
See application file for complete search history.

(56) References Cited

U.S. PATENT DOCUMENTS

2002/0081734 A1* 6/2002 Choi .................... C07K 14/505
435/455
2006/0252051 A1* 11/2006 Merryman ............. C07H 21/00
435/6.12
2013/0217599 A1 8/2013 Suga et al.

FOREIGN PATENT DOCUMENTS

EP          2610348 A1    7/2013
JP       2007-319064 A   12/2007
WO       2012026566 A1    3/2012

OTHER PUBLICATIONS

Roberts et al (Current Opinion in Chemical Biology 3:268-73) (Year: 1999).*
Gilmore et al (Topics in Current Chemistry 202:77-99) (Year: 1999).*
Bain, et al., "Site-specific incorporation of non-natural residues into peptides: Effect of residue structure on suppression and translation efficiencies", Mar. 8, 2001, pp. 2389-2400, vol. 47, No. 14-15, Publisher: Tetrahedron.
Choudhury, et al., "Synthesis of Proteins Containing Modified Arginine Residues", Mar. 9, 2007, pp. 4066-4076, vol. 46, Publisher: Biochemistry.
Chung, et al., "Probing the role of loop 2 in Ras function with unnatural amino acids", Nov. 1, 1993, pp. 10145-10149, vol. 90, No. 21, Publisher: Proc Natl Acad Sci USA.
Chung, et al., "Probing the Structure and Mechanism of Ras Protein with an Expanded Genetic Code", Feb. 5, 1993, pp. 806-809, vol. 259, Publisher: Science.
Ellman, et al., "Site-Specific Incorporation of Novel Backbone Structures into Proteins", Jan. 10, 1992, pp. 197-200, vol. 255, Publisher: Science.
International Search Report received in PCT/JP2014/070487, dated Nov. 4, 2014.
Karginov, et al., "Probing the Role of an Active Site Aspartic Acid in Dihydrofolate Reductase", Aug. 15, 1997, pp. 8166-8176, vol. 119, No. 35, Publisher: J. Am. Chem. Soc.
Kawakami, et al., "Genetically Encoded Libraries of Nonstandard Peptides", Oct. 14, 2012, pp. 1-15, vol. 2012, No. 713510, Publisher: Journal of Nucleic Acids.

(Continued)

*Primary Examiner* — Christopher M Gross
(74) *Attorney, Agent, or Firm* — Suzannah K. Sundby, Esq.; Canady + Lortz LLP

(57) ABSTRACT

An object of the present invention is to provide a method of producing a peptide containing a charged non-proteinogenic amino acid in a cell-free translation system, and the like.

The present invention provides a method of producing a peptide containing a charged non-proteinogenic amino acid. It includes a step of expressing a peptide in a cell-free translation system including (i) at least one tRNA to which a non-proteinogenic amino acid having a protecting-group-introduced charged group has been bound and (ii) a nucleic acid that encodes the peptide and contains at least one codon corresponding to an anticodon of the tRNA; and a step of removing the protecting group of the non-proteinogenic amino acid residue contained in the peptide.

6 Claims, 9 Drawing Sheets
Specification includes a Sequence Listing.

(56) References Cited

OTHER PUBLICATIONS

Schlippe, et al., "In Vitro Selection of Highly Modified Cyclic Peptides That Act as Tight Binding Inhibitors", Mar. 19, 2012, pp. 1046910477, vol. 134, Publisher: J. Am. Chem. Soc.

Short, et al., "Probing the S1/S1 Substrate Binding Pocket Geometry of HIV-1 Protease with Modified Aspartic Acids Analogues", Jul. 6, 2000, pp. 8768-8781, vol. 39, Publisher: Biochemistry.

Written Opinion received in PCT/JP2014/070487, dated Nov. 4, 2014.

Yamagishi, et al., "Natural Product-Like Macrocyclic N-Methyl-Peptide Inhibitors against a Ubiquitin Ligase Uncovered from a Ribosome-Expressed De Novo Library", Dec. 23, 2011, pp. 15621570, vol. 18, Publisher: Chemistry & Biology.

Goto, et al., "Initiating translation with D-amino acids", Jul. 1, 2008, pp. 1390-1398, vol. 14, No. 7, Publisher: RNA.

Goto, et al., "Flexizymes for genetic code reprogramming", May 12, 2011, pp. 779790, vol. 6, Publisher: Nature Protocols.

* cited by examiner

PRODUCTION METHOD FOR CHARGED NON-PROTEIN AMINO ACID-CONTAINING PEPTIDE

Reference to a Sequence Listing Submitted via EFS-Web

The content of the ASCII text file of the sequence listing named "20160204 034574 008US1 seq", which is 2.53 kb in size and electronically submitted on on Feb. 4, 2016, via EFS-Web, is incorporated herein by reference in its entirety.

TECHNICAL FIELD

The present invention relates to a method of producing a charged non-proteinogenic amino acid-containing peptide in a cell-free translation system, and the like.

BACKGROUND ART

In recent years, various peptides have attracted attention as a drug candidate or research tool and there have been attempts to develop a peptide library and screen peptides having affinity to a target substance.

For artificial creation of a peptide library, a chemical synthesis method, a method using a biosynthesis enzyme of a secondary metabolite, a method using a translation synthesis system, or the like has conventionally been used.

The chemical synthesis method has difficulty in enhancing diversity of a library. In addition, this method needs much time for screening or for analysis of correlation between the structure and activity of a compound.

The method using a biosynthesis enzyme of a secondary metabolite, on the other hand, permits rapid and easy construction of an elaborate skeleton or chemical conversion. This method is however not suited for construction of a large-scale compound library because kinds of compounds that can be synthesized by this method are limited due to substrate specificity of the enzyme.

When the translation synthesis system is used, a peptide library rich in variety can be constructed in a short time by creating an mRNA library and translating it. In addition, by using it in combination with an mRNA display method or the like, nucleic acid molecules which are genotype molecules and peptides which are phenotype molecules can be correlated to each other, making it possible to rapidly and easily searching and concentrating peptides that bind to a desired target molecule from the library. Thus, using a translation system for the synthesis of a peptide library has many advantages, but it is almost limited to production of peptides composed of a proteinogenic amino acid.

In particular, the present inventors have elucidated that when a peptide is synthesized in in vitro translation system, it is very difficult to incorporate a non-proteinogenic amino acid bearing an electrically charged side chain. Similarly, it is reported that with regard to incorporation of an N-alkyl amino acid in protein by nonsense suppression in a translation system using a cell extract, an incorporation efficiency of a charged N-alkyl amino acid is markedly low (Non-patent Documents 1 to 3) and an incorporation efficiency of a non-charged N-alkyl amino acid is high (Non-patent Documents 4 to 7).

According to recent reports, some non-charged N-alkyl amino acids are suitably used in in vitro peptide selection (Reference Documents 8 to 10), but structural diversity of charged non-proteinogenic amino acids that can be incorporated in a peptide by ribosomal synthesis has still been limited.

It is therefore presumed that the structural diversity of a peptide library that can be used for in vitro peptide selection can be enhanced markedly if a charged non-proteinogenic amino acid is incorporated in a peptide by ribosomal synthesis.

CITATION LIST

Non-Patent Document

Non-Patent Document 1: Karginov, V. A. et al. J. Am. Chem. Soc. 119, 8166-8176 (1997).
Non-Patent Document 2: Short, G. F., 3rd et al. Biochemistry 39, 8768-8781 (2000).
Non-Patent Document 3: Choudhury, A. K., Golovine, S. Y., Dedkova, L. M. & Hecht, S. M. Biochemistry 46, 4066-4076 (2007).
Non-Patent Document 4: Bain, J. D., Wacker, D. A., Kuo, E. E. & Chamberlin, A. R. Tetrahedron 47, 2389-2400 (1991).
Non-Patent Document 5: Ellman, J. A., Mendel, D. & Schultz, P. G. Science 255, 197-200 (1992).
Non-Patent Document 6: Chung, H. H., Benson, D. R., Cornish, V. W. & Schultz, P. G. Proc. Natl. Acad. Sci. USA 90, 10145-10149 (1993).
Non-Patent Document 7: Chung, H. H., Benson, D. R. & Schultz, P. G. Science 259, 806-809 (1993).
Non-Patent Document 8: Yamagishi, Y. et al. Chem. Biol. 18, 1562-1570 (2011).
Non-Patent Document 9: Kawakami, T. & Murakami, H. J. Nucleic Acids 2012, 713510 (2012).
Non-Patent Document 10: Schlippe, Y. V., Hartman, M. C., Josephson, K. & Szostak, J. W. J. Am. Chem. Soc. 134, 10469-10477 (2012).

SUMMARY

Technical Problem

An object of the present invention is to provide a method of producing a peptide containing a charged non-proteinogenic amino acid in a cell-free translation system, and the like.

Solution to Problem

The present inventors have found that even if a non-proteinogenic amino acid has a positive or negative charge, when a peptide is expressed in a cell-free translation system obtained by introducing a protecting group into the charged group, binding the resulting amino acid to tRNA, and adding the resulting protecting-group-introduced aminoacyl tRNA, the protecting-group-introduced amino acid is efficiently incorporated in the peptide and that by carrying out deprotection after translation and thereby exposing the charged group, a charged non-proteinogenic amino acid-containing peptide can be produced.

Further, finding that when a peptide is expressed in a cell-free translation system to which a protecting-group-introduced aminoacyl tRNA has been added, while using a puromycin linker-bound mRNA as a template, a peptide containing a protecting-group-introduced amino acid is displayed on mRNA, the present inventors have confirmed that the above-described method of producing a charged non-proteinogenic amino acid-containing peptide can be used for in vitro display method and have completed the present invention.

Described specifically, the present invention relates to:

[1] a method of producing a charged non-proteinogenic amino acid-containing peptide having:

a step of expressing a peptide in a cell-free translation system including:

(i) at least one tRNA to which a non-proteinogenic amino acid having a protecting-group-introduced charged group has been bound, and (ii) a nucleic acid that encodes the peptide and contains at least one codon corresponding to an anticodon of the tRNA; and a step of removing the protecting group of a non-proteinogenic amino acid residue contained in the peptide;

[2] a method of producing a peptide library including charged non-proteinogenic amino acid-containing peptides, having:

a step of expressing a peptide library in a cell-free translation system including:

(i) at least one tRNA to which a non-proteinogenic amino acid having a protecting-group-introduced charged group has been bound, and (ii) a nucleic acid library that encodes the peptide library, each nucleic acid containing at least one codon corresponding to an anticodon of the tRNA; and a step of removing the protecting group of a non-proteinogenic amino acid residue contained in peptides of the peptide library;

[3] the producing method as described above in [1] or [2], wherein the charged group is an amino group or a carboxyl group;

[4] the producing method as described above in [1] or [2], wherein the charged group is an amino group and the protecting group is an azide group;

[5] the producing method as described above in [1] or [2], wherein the charged group is a carboxyl group and the protecting group is an alkyl ester group or an aralkyl ester group;

[6] a cell-free translation system for producing a charged non-proteinogenic amino acid-containing peptide, having:

(i) at least one tRNA to which a non-proteinogenic amino acid having a protecting-group-introduced charged group has been bound, and (ii) a nucleic acid that encodes the peptide and contains at least one codon corresponding to an anticodon of the tRNA;

[7] a cell-free translation system for producing a peptide library including charged non-proteinogenic amino acid-containing peptides, having:

(i) at least one tRNA to which a non-proteinogenic amino acid having a protecting-group-introduced charged group has been bound, and (ii) a nucleic acid library that encodes the peptide library, each nucleic acid containing at least one codon corresponding to an anticodon of the tRNA;

[8] the translation system as described above in [6] or [7], wherein the charged group is an amino group or a carboxyl group;

[9] the translation system as described above in [6] or [7], wherein the charged group is an amino group and the protecting group is an azide group;

[10] the translation system as described above in [6] or [7], wherein the charged group is a carboxyl group and the protecting group is an alkyl ester group or an aralkyl ester group;

[11] an in vitro selection method using a peptide library including charged non-proteinogenic amino acid-containing peptides, which has:

a) a step of expressing a peptide-mRNA complex library in a cell-free translation system including at least one tRNA to which a non-proteinogenic amino acid having a protecting-group-introduced charged group has been bound and an mRNA library that encodes each of peptides of the peptide library, each mRNA containing at least one codon corresponding to an anticodon of the tRNA and having puromycin bound to a region downstream of ORF of the mRNA;

b) a step of subjecting the peptide-mRNA complex library to a reverse transcription reaction to obtain a peptide-DNA complex library;

c) a step of removing the protecting group of the charged group;

d) a step of selecting a group of peptide-DNA complexes that bind to a target substance from the peptide-DNA complex library;

e) a step of amplifying the DNA of the selected peptide-DNA complex group; and;

f) transcribing the amplified DNA to construct an mRNA library, binding puromycin to the downstream region of ORF of each mRNA to obtain a puromycin-bound mRNA library, and translating the library into a peptide-mRNA library;

wherein a peptide having high affinity to the target substance is selected by carrying out the steps from a) to f) once or twice or more;

[12] an in vitro selection method using a peptide library including charged non-proteinogenic amino acid-containing peptides, which has:

a) a step of expressing a peptide-mRNA complex library in a cell-free translation system including at least one tRNA to which a non-proteinogenic amino acid having a protecting-group-introduced charged group has been bound and an mRNA library that encodes each of the peptides of the peptide library, each mRNA containing at least one codon corresponding to an anticodon of the tRNA and having puromycin bound to a region downstream of ORF of the mRNA, b) a step of removing the protecting group of the charged group;

c) a step of subjecting the peptide-mRNA complex library to a reverse transcription reaction to obtain a peptide-DNA complex library;

d) a step of selecting a group of peptide-DNA complexes that bind to a target substance from the peptide-mRNA complex library;

e) a step of amplifying the DNA of the selected peptide-DNA complex group; and f) transcribing the amplified DNA to construct an mRNA library, binding puromycin to the downstream region of ORF of each mRNA to obtain a puromycin-bound mRNA library, and translating the library into a peptide-mRNA library;

wherein a peptide having high affinity to the target substance is selected by carrying out the steps from a) to f) once or twice or more;

[13] an in vitro selection method using a peptide library including charged non-proteinogenic amino acid-containing peptides, which has:

a) a step of expressing a peptide-mRNA complex library in a cell-free translation system including at least one tRNA to which a non-proteinogenic amino acid having a protecting-group-introduced charged group has been bound and an mRNA library that encodes peptides of the peptide library, each mRNA containing at least one codon corresponding to an anticodon of the tRNA and having puromycin bound to a region downstream of ORF of the mRNA;

b) a step of removing the protecting group of the charged group;

c) a step of selecting a group of peptide-mRNA complexes that bind to a target substance from the peptide-mRNA complex library;

d) a step of subjecting the peptide-mRNA complex library to a reverse transcription reaction to obtain a peptide-DNA complex library;

e) a step of amplifying the DNA of the selected peptide-DNA complex group; and;

f) transcribing the amplified DNA to construct an mRNA library, binding puromycin to the downstream region of ORF of each mRNA to obtain a puromycin-bound mRNA library, and translating the library into a peptide-mRNA library;

wherein a peptide having high affinity to the target substance is selected by carrying out the steps from a) to f) once or twice or more.

Advantageous Effects of Invention

According to the production method and cell-free translation system of the present invention, peptides having a charged non-proteinogenic amino acid can be produced efficiently in a cell-free translation system. In addition, by using this method, a peptide library composed of peptides containing a charged non-proteinogenic amino acid can be obtained.

Many peptides containing a charged non-proteinogenic amino acid are excellent in protease resistance or cell membrane permeability and can be a drug candidate equipped with such a property. A peptide library including the charged non-proteinogenic amino acid is suitably used for screening of a drug candidate equipped with such a property. In this point, the production method of the present invention can be used also for selection by various in vitro display methods.

DESCRIPTION OF EMBODIMENTS

[Production Method of Peptide]

Figure 1:
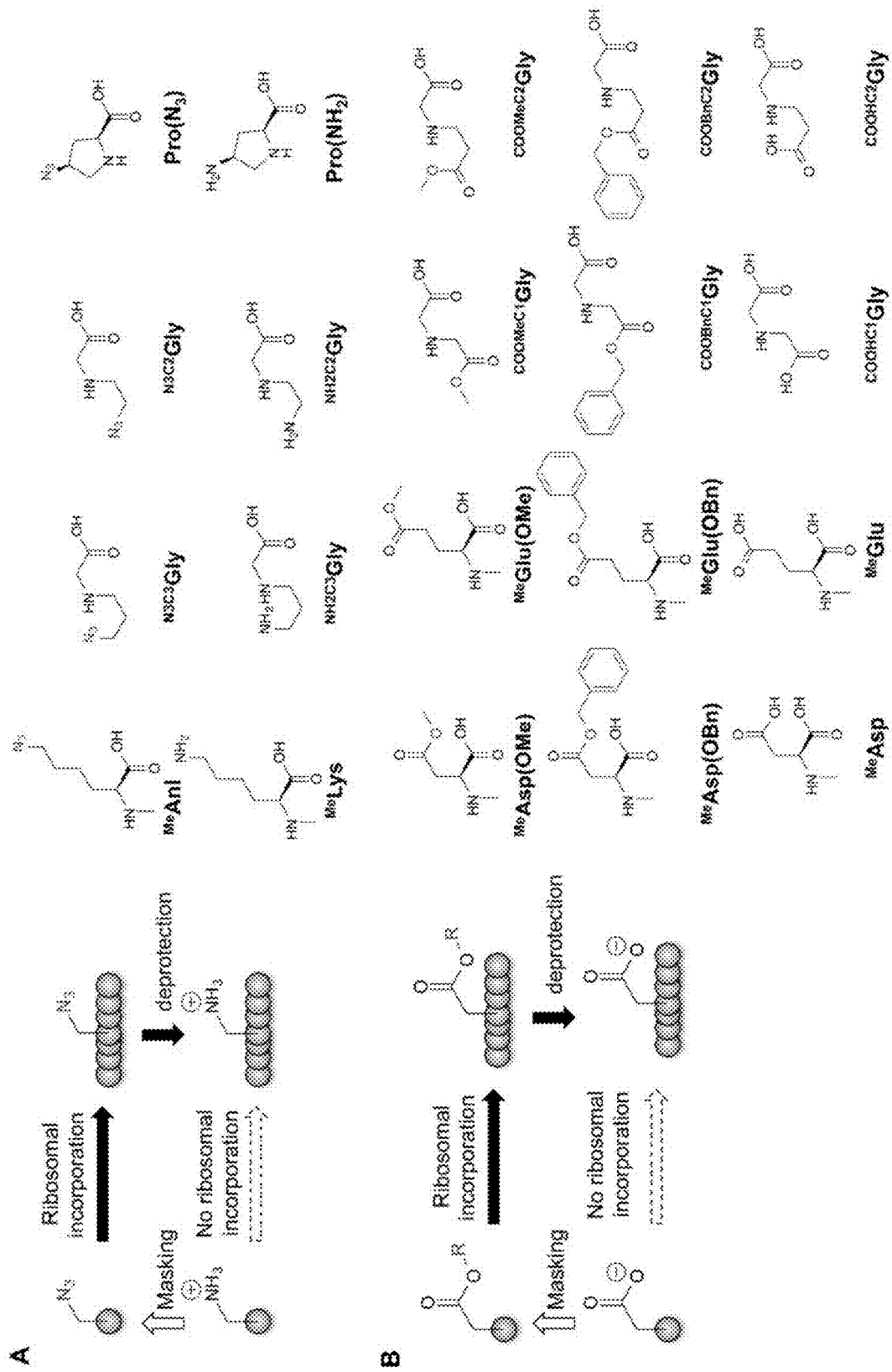
FIG. 1 shows ribosomal incorporation schemes of a charged N-alkyl amino acid in a peptide according to the method of the present invention. (A) shows the outline of ribosomal incorporation of a positively charged N-alkyl amino acid in a peptide and the structure of N-alkyl amino acids used for experiment. An N-alkyl amino acid precursor containing an azide group that masked the positive charge of a translation unsuitable amine-containing N-alkyl amino acid was ribosomally incorporated in a peptide. The azide group of the peptide is chemically converted into an amino group by a trialkyl phosphine after translation and becomes an amine-containing N-alkyl amino acid residue in the peptide. In the scheme, $^{Me}$Lys represents Nα-methyl-L-lysine; $^{NH2C3}$Gly represents N-(3-aminopropyl)-glycine, $^{NH2C3}$Gly represents N-(2-aminoethyl)-glycine, Pro (NH$_2$) represents cis-4-amino-L-proline; $^{Me}$Anl represents 6-azido-N-methyl-L-norleucine; $^{N3C3}$Gly represents N-(3-azidopropyl)-glycine; $^{N3C3}$Gly represents N-(2-azidoethyl)-glycine; and Pro(N3) represents cis-4-azido-L-proline. (B) shows the outline of ribosomal incorporation of a negatively charged N-alkyl amino acid in a peptide and the structure of N-alkyl amino acids used for experiment. Negatively-charged carboxyl-containing N-alkyl amino acids are unsuitable for translation. These N-alkyl amino acid precursors can be ribosomally incorporated in a peptide by esterifying the carboxyl group. This ester group can be enzymatically converted into a carboxyl group with carboxyl esterase after translation. In the scheme, $^{Me}$Asp represents N-methyl-L-aspartic acid; $^{Me}$Glu represents N-methyl-L-glutamic acid; $^{COOHC2}$Gly represents N-(2-carboxylethyl)-glycine; $^{COOHC1}$Gly represents N-carboxylmethyl-glycine; $^{Me}$Asp(OMe) represents N-methyl-L-aspartic acid O-methyl ester; $^{Me}$Glu(OMe) represents N-methyl-L-glutamic acid O-methyl ester; $^{COOMeC2}$Gly represents N-(2-carboxylethyl)-glycine O-methyl ester; $^{COOMeC1}$Gly represents N-carboxylmethyl-glycine O-methyl ester; $^{Me}$Asp (OBn) represents N-methyl-L-aspartic acid O-benzyl ester; $^{Me}$Glu(OMe) represents N-methyl-L-glutamic acid O-benzyl ester; $^{COOMeC2}$Gly represents N-(2-carboxylethyl)-glycine O-benzyl ester; and $^{COOMeC1}$Gly represents N-carboxylmethyl-glycine O-benzyl ester.

The method of producing a charged non-proteinogenic amino acid containing peptide according to the present invention includes:

a step of expressing a peptide in a cell-free translation system including:

(i) at least one tRNA to which a non-proteinogenic amino acid having a protecting-group-introduced charged group and (ii) a nucleic acid that encodes the peptide and contains at least one codon corresponding to an anticodon of the tRNA; and a step of removing the protecting group of a non-proteinogenic amino acid residue contained in the peptide.

In the present specification, the term "amino acid" is used in its broadest meaning and it embraces not only natural amino acids but also artificial amino acid variants and derivatives of them. The amino acids may be represented by commonly used single-letter or three-letter codes, respectively. Examples of the amino acid or derivatives thereof used herein include natural proteinogenic L-amino acids, unnatural amino acids, and chemically synthesized compounds having properties known in the art as characteristics of an amino acid. Examples of the unnatural amino acids include, but not limited to, α,α-disubstituted amino acids (such as α-methylalanine), N-alkyl-α-amino acids, D-amino acids, β-amino acids, and α-hydroxy acids, each having a main chain structure different from that of natural amino acids; amino acids (such as norleucine and homohistidine) having a side-chain structure different from that of natural amino acids; amino acids (such as "homo" amino acids, homophenylalanine, and homohistidine) having extra methylene in the side chain thereof; and amino acids (such as cysteic acid) obtained by substituting a carboxylic acid functional group amino acid in the side chain thereof by a sulfonic acid group.

The amino acids embrace proteinogenic amino acids and non-proteinogenic amino acids.

The term "proteinogenic amino acid" as used herein means an amino acid (Arg, His, Lys, Asp, Glu, Ser, Thr, Asn, Gin, Cys, Gly, Pro, Ala, lie, Leu, Met, Phe, Trp, Tyr, or Val) constituting a protein.

The term "non-proteinogenic amino acid" as used herein means a natural or unnatural amino acid other than the proteinogenic amino acid.

The term "charged amino acid" as used herein means an amino acid that may be ionized when introduced into a peptide or protein, in other words, an amino acid having a positively or negatively charged group in a near neutral aqueous solution. The positively charged group is typically an amino group and the negatively charged group is typically a carboxyl group, but they are not limited to such groups, respectively. Examples of the other charged group include an imidazole group, a guanidino group, a phosphoric acid group, a sulfo group, and a pyridinium group, and these groups modified (modified by alkylation, methylation, or demethylation).

The term "charged non-proteinogenic amino acid" as used herein means a non-proteinogenic amino acid having a functional group that is ionized partially at near neutral pH while being introduced into a protein or peptide.

Examples of positively charged non-proteinogenic amino acids include $^{Me}$Lys, $^{NH2C3}$Gly, $^{NH2C2}$Gly, and Pro(NH$_2$) and examples of negatively charged non-proteinogenic amino acids include N-alkylamino acids such as $^{Me}$Asp, $^{Me}$Glu, $^{COOHC1}$Gly, and $^{COOHC2}$Gly. Additional examples include, but not limited to, D-amino acids and β-amino acids having a charged group.

The term "peptide" as used herein means a compound in which from 2 to 100, from 3 to 80, or from 5 to 30 amino acids have been bound via peptide bonding. The term "charged non-proteinogenic amino acid-containing peptide" as used herein means a peptide containing at least one charged non-proteinogenic amino acid. The number of charged non-proteinogenic amino acids is not particularly limited and examples of the number may include two, three, four, five, six, seven, eight, nine, and ten. In a peptide containing at least two charged non-proteinogenic amino acids, these charged non-proteinogenic amino acids may be successive or may have another amino acid such as proteinogenic amino acid between them.

The "protecting group" to be introduced into a charged group of the charged non-proteinogenic amino acid in the present specification is any group insofar as it is a protecting group that masks the charge of the charged group and is selected as needed, depending on the kind of the charged group. For example, when the charged group is an amino group, various known amino protecting groups can be used. Preferable examples include an Alloc group, a Troc group, an Ns group, a Boc group, an Fmoc group, a Cbz group, a Pht group, a Ts group, and various acyl groups and those resulting in an azide group ($-N_3$) or a sulfonamide group as the protecting-group-introduced charged group. When the charged group is a carboxyl group, various known carboxyl protecting groups can be used. Preferable examples include those resulting in alkyl ester groups (lower alkyl esters, for example, methyl esters, ethyl esters, isopropyl esters, and butyl esters) and aralkyl esters groups (for example, benzyl esters) as the protecting-group-introduced charged group.

As the protecting group, those chemically or enzymatically removable under relatively mild conditions are preferred.

The term "tRNA to which a non-proteinogenic amino acid having a protecting-group-introduced charged group has been bound" as used herein means a tRNA having a 3' end to which a non-proteinogenic amino acid having a protecting-group-introduced charged group has been bound.

A method of binding a non-proteinogenic amino acid having a protecting-group-introduced charged group to tRNA is not particularly limited, but, for example, artificial aminoacylation RNA catalyst flexizyme can be used (WO2007/066627, WO2012/026566). Flexizyme is an artificial RNA catalyst (an RNA catalyst having an acyl tRNA synthase-like activity) capable of coupling (acylating) an arbitrary amino acid, hydroxy acid, or carboxylic acid to an arbitrary tRNA.

As flexizyme, for example, those described in the following documents are known: H. Murakami, H. Saito, and H. Suga, (2003), Chemistry & Biology, Vol. 10, 655-662; H. Murakami, D. Kourouklis, and H. Suga, (2003), Chemistry & Biology, Vol. 10, 1077-1084; H. Murakami, A. Ohta, H. Ashigai, H. Suga (2006) Nature Methods 3, 357-359; N. Niwa, Y. Yamagishi, H. Murakami, H. Suga (2009) Bioorganic & Medicinal Chemistry Letters 19, 3892-3894; and WO2007/066627 "Multi-purpose acylation catalyst and use thereof". As flexizyme, original flexizyme (Fx) and altered ones thereof such as dinitrobenzyl flexizyme (dFx), enhanced flexizyme (eFx), and aminoflexizyme (aFx) are also known.

In a reconstituted translation system, using flexizyme instead of aminoacyl tRNA which is synthesized by a natural aminoacyl tRNA synthase makes it possible to rewrite a genetic code table by corresponding a desired amino acid, hydroxy acid, or carboxylic acid different from that of a natural genetic code to an arbitrary codon. This is called codon reassignment.

The term "reconstituted translation system" as used herein means a cell-free translation system which can be reconstituted from necessary components left after free removal of constituent factors of a translation system according to purpose. For example, when a translation system from which a specific amino acid has been removed is reconstituted, a codon corresponding to the amino acid becomes an empty codon that does not encode any amino acid.

When an arbitrary amino acid, hydroxy acid, carboxylic acid, or the like is coupled to a tRNA having an anticodon complementary to the empty codon by using flexizyme or the like and translation is performed by adding it, the arbitrary amino acid, hydroxy acid, carboxylic acid, or the like is encoded by the codon and a peptide having the arbitrary amino acid, hydroxy acid, carboxylic acid, or the like introduced instead of the removed amino acid is translated.

In the present invention, by binding the protecting-group-introduced non-proteinogenic amino acid to a tRNA having an anticodon complementary to the empty codon, the non-proteinogenic amino acid can be incorporated in an arbitrary position of the peptide.

The tRNA to be used in the present invention may be an *Escherichia coli* derived wild type tRNA or an artificial tRNA prepared by in vitro transcription.

When there are two non-proteinogenic amino acids having a protecting-group-introduced charged group, tRNAs to be coupled to the respective amino acids may be different from each other or may have identical sequences except for an anticodon loop portion.

The term "cell-free translation system" as used herein means a translation system not including cells. As the cell-free translation system, for example, an *Escherichia coli* extract, a wheat germ extract, a rabbit reticulocyte extract, or an insect cell extract can be used. In the present invention, a reconstituted cell-free translation system may be used, which is obtained by reconstituting a purified ribosome protein, aminoacyl tRNA synthase (aaRS), ribosomal RNA, amino acid, rRNA, GTP, ATP, translation initiation factor (IF), elongation factor (EF), release factor (RF), and ribosome regeneration factor (RRF), and another factor necessary for translation. The system may include RNA polymerase for performing transcription from DNA simultaneously.

Examples of a commercially available cell-free translation system usable here include *Escherichia-coli* derived systems such as "RTS-100" (trade mark) of Roche Diagnostics, reconstituted translation systems such as "PURESYSTEM" (trade mark) of PGI and "PURExpressR In Vitro Protein Synthesis Kit" of New England Biolabs, and systems using a wheat germ extract such as those of ZOEGENE Corporation or CellFree Sciences.

As a system using a ribosome of *Escherichia coli*, for example, a technology described in the following documents is known. H. F. Kung et al., 1977. The Journal of Biological Chemistry Vol. 252, No. 19, 6889-6894; M. C. Gonza et al., 1985, Proceeding of National Academy of Sciences of the United States of America Vol. 82, 1648-1652; M. Y. Pavlov and M. Ehrenberg, 1996, Archives of Biochemistry and Biophysics Vol. 328, No. 1, 9-16; Y. Shimizu et al., 2001, Nature Biotechnology Vol. 19, No. 8, 751-755; H. Ohashi et al., 2007, Biochemical and Biophysical Research Communications Vol. 352, No. 1, 270-276.

By using the cell-free translation system, a high-purity expression product can be obtained without purifying.

The cell-free translation system to be used for the method of producing a charged non-proteinogenic amino acid-containing peptide according to the present invention includes (i) at least one tRNA to which a protecting-group-introduced non-proteinogenic amino acid has been bound and (ii) a nucleic acid encoding the peptide and containing at least one codon corresponding to an anticodon of the tRNA.

The nucleic acid encoding the peptide and containing at least one codon corresponding to an anticodon of the tRNA may be either DNA or RNA. When it is DNA, RNA polymerase is added to the cell-free translation system as described above to cause a transcription reaction.

Such a nucleic acid can be prepared as needed by the method known to those skilled in the art or a method based thereon.

The "step of expressing a peptide" in this specification can be performed by incubating, under appropriate condition, a cell-translation system including (i) at least one tRNA to which a non-proteinogenic amino acid having a protecting-group-introduced charged group has been bound and (ii) a nucleic acid encoding the peptide and containing at least one codon corresponding to an anticodon of the tRNA.

To the cell-free translation system, an elongator tRNA or initiator tRNA to which an amino acid other than the non-proteinogenic amino acid having a protecting-group-introduced charged group and encoded by the above-described nucleic acid, and another necessary component may be added as needed.

The "step of removing a protecting group of the non-proteinogenic amino acid residue contained in the peptide" can be performed by a method known to those skilled in the art or a method based thereon, depending on the kind of the protecting group. The protecting group can be removed chemically or enzymatically by adding a necessary compound or enzyme to the cell-free translation system and incubating the mixture under appropriate conditions.

For example, removal of an azide group can be achieved by adding tris(2-carboxyethyl)phosphine (TCEP) to a translation product and then incubating the resulting mixture at 42° C. and pH 8.4 for from 10 to 60 minutes. Removal of an alkyl ester or aralkyl ester can be performed by adding carboxylesterase to a translation product and then incubating the resulting mixture at 42° C. and pH 8.4 for from 12 to 24 hours.

By this step, the charged group of the charged amino acid is exposed and as a result, a charged non-proteinogenic amino acid-containing peptide can be obtained.

[Production Method of Peptide Library]

By using the method of producing a peptide according to the present invention, a peptide library including charged non-proteinogenic amino acid-containing peptides can also be produced.

The method of producing a peptide library according to the present invention is similar to the method of producing a peptide according to the present invention except that a nucleic acid library encoding a peptide library, instead of a nucleic acid encoding a peptide, is added to a cell-free translation system.

The nucleic acid library encoding a peptide library can be prepared by a method known to those skilled in the art or based on it. When each nucleic acid of the nucleic acid library includes a random sequence and the random sequence includes a codon to an anticodon of a tRNA to which a non-proteinogenic amino acid having a protecting-group-introduced charged group has been bound, the non-proteinogenic amino acid is incorporated.

The peptide library thus obtained is a highly functional library of peptides each containing a charged non-proteinogenic amino acid. The peptides can have improved membrane permeability or protease resistance, depending on the kind of the charged non-proteinogenic amino acid so that the resulting peptide library is useful for screening of a drug candidate.

The peptide or peptide library produced by the method according to the present invention may be macrocyclized. The term "macrocyclize" as used herein means that within one peptide, two amino acids separated from each other with a distance corresponding to one or more amino acids are bound to each other directly or indirectly via a linker or the like and thereby form a macrocyclic structure in the molecule.

The peptide can be macrocyclized by disulfide bonding, peptide bonding, alkyl bonding, alkenyl bonding, ester bonding, thioester bonding, ether bonding, thioether bonding, phosphonate ether bonding, azo bonding, C—S—C bonding, C—N—C bonding, C=N—C bonding, amide bonding, lactam bridging, carbamoyl bonding, urea bonding, thiourea bonding, amine bonding, thioamide bonding, or the like, but bonding is not limited to them.

The peptides thus macrocyclized may have a stable structure and have enhanced affinity to a target.

For cyclization, for example, a chloroacetylated amino acid may be placed at the N terminal and Cys may be placed at the C terminal. After peptides are expressed, they are naturally cyclized by thioether bonding between the N-terminal amino acid and the C terminal Cys. The thioether bond formed between the chloroacetylated amino acid and the Cys is not susceptible to degradation under reducing conditions in vivo so that it is possible to increase the half-life of the peptide in blood and thereby keep its bioactive effect.

Examples of the chloroacetylated amino acid include N-chloroacetyl-L-alanine, N-chloroacetyl-L-phenylalanine, N-chloroacetyl-L-tyrosine, N-chloroacetyl-L-tryptophan, N-3-chloromethylbenzoyl-L-phenylalanine, N-3-chloromethylbenzoyl-L-tyrosine, N-3-chloromethylbenzoyl-L-tryptophane, N-3-(2-chloroacetamido)benzoyl-L-phenylalanine, N-3-(2-chloroacetamido)benzoyl-L-tyrosine, N-3-(2-chloroacetamido)benzoyl-L-tryptophane, and D-amino acid derivatives corresponding to them.

Using, as the chloroacetylated amino acid, Nγ-(2-chloroacetyl)-α,γ-diaminobutylic acid or Nγ-(2-chloroacetyl)-α,γ-diaminopropanoic acid enables introduction in any site of the peptide chain so that a thioether bond is formed between the amino acid at any position and cysteine in the same peptide to form a cyclic structure.

The macrocyclization method can be carried out in accordance with a method described, for example, in Kawakami, T. et al., Nature Chemical Biology 5, 888-890 (2009); Yamagishi, Y. et al., ChemBioChem 10, 1469-1472 (2009); Sako, Y. et al., Journal of American Chemical Society 130, 7932-7934 (2008); Goto, Y. et al., ACS Chemical Biology 3, 120-129 (2008); or Kawakami T. et al, Chemistry & Biology 15, 32-42 (2008).

The chloroacetylated amino acid and Cys may be bound to the peptide of the present invention either directly or via a linker or the like.

[In Vitro Display]

The present invention embraces an in vitro selection method to be used for a peptide library including charged non-proteinogenic amino-acid containing peptides.

The in vitro display method of the present invention is performed similarly to the method of producing a peptide library according to the present invention except that instead of the mRNA library encoding a peptide, a puromycin-bound mRNA library obtained by binding puromycin to a downstream region of ORF of each mRNA is added to the cell-free translation system. The puromycin may be bound to mRNA via a linker composed of a peptides or nucleic acid. By binding puromycin to the region downstream of ORF of each mRNA, a ribosome that has translated the ORF of mRNA incorporates puromycin therein and an mRNA-peptide complex is formed. In such a peptide-mRNA complex, genotype and phenotype can be corresponded to each other.

Then, a reverse transcription reaction of the peptide-mRNA complex is performed to obtain a peptide-DNA complex library. This step can be achieved by adding a reverse transcriptase and incubating the resulting mixture as needed.

After the reverse transcription reaction, the non-proteinogenic amino acid residue having a protecting-group-introduced charged group is deprotected to expose the charged group of the charged non-proteinogenic amino acid.

The peptide may be macrocyclized prior to a reaction with a target substance.

Next, from the peptide-DNA complex library, a group of peptide-DNA complexes that bind to a target substance is selected.

In the above method, after translation, reverse transcription reaction, removal of the protecting group, and selection of a group of peptide-DNA complexes that bind to a target substance are performed in the order of mention. It is also possible to, after translation, remove the protecting group and then carry out a reverse transcription reaction and selection of a group of peptide-DNA complexes that bind to a target substance; or to, after translation, remove the protecting group, select a group of peptide-mRNA complexes that bind to a target substance, and then carry out a reverse transcription reaction.

The "target substance" is not particularly limited in the present specification and examples include low molecular compounds, high molecular compounds, nucleic acids, peptides, proteins, sugars, and lipids. In particular, the library of the present invention can be used also when the target substance has protease activity or it is an intracellular molecule.

The target substance immobilized onto, for example, a solid-phase support may be brought into contact with the library of the present invention. The term "solid-phase support" as used herein is not particularly limited insofar as it can immobilize the target substance thereonto. Examples include microtiter plates, substrates, and beads made of glass, a metal, a resin, or the like, nitrocellulose membranes, nylon membranes, and PVDF membranes. The target substance can be immobilized onto such a solid phase support in a known manner.

The target substance and the library are brought into contact with each other in a buffer selected as needed and they are interacted while controlling pH, temperature, time, and the like. Then, the solid phase surface is washed to elute the peptide-DNA complex bound to the solid phase surface with a buffer. Thus, a group of peptide-DNA complexes that bind to the target substance can be selected.

The DNA of the group of peptide-DNA complexes thus obtained is amplified. The amplification step can be performed by PCR.

Since an mRNA library encoding a group of peptides that bind to the target substance can be obtained by the transcription of the amplified DNA, puromycin can be bound to the library to obtain a puromycin-bound mRNA library. The resulting puromycin-bound mRNA library encodes a group of peptides having affinity to the target substance higher than that of the puromycin-bound mRNA library obtained first. It is therefore possible to concentrate a peptide having higher affinity to the target substance and a nucleic acid encoding it by repeating the above-described step.

Peptides that bind to the target substance are likely to show various activities through inhibition of the activity of the target substance so that they are useful as a drug or diagnostic agent candidate.

The present invention also provides a peptide screening kit.

One mode of the screening kit of the present invention includes the peptide library or peptide-mRNA complex library produced by the production method according to the present invention.

The screening kit of the present invention includes, in addition, a reagent and an apparatus necessary for detecting the binding between a target substance and a peptide or peptide-mRNA complex. Examples of such a reagent and apparatus include, but not limited to, solid phase supports, buffers, labeling reagents, enzymes, enzyme reaction terminator solutions, and microplate readers.

The complete disclosure of the patent documents and non-patent documents cited herein are incorporated herein by reference in their entirety.

EXAMPLES

The present invention will hereinafter be described specifically based on Examples, but the present invention is not limited to or by them. Those skilled in the art can change the present invention into various modes without departing from the gist of the present invention and such a change is also embraced within the scope of the present invention.

1. Material and Method 1-1. Ribosomal Synthesis of Charged N-Alkyl Amino Acid-Containing Peptide Preparation of a translation system, a DNA template encoding a peptide, and preparation of an N-alkylamino acyl-tRNA$^{Asn-E2}_{GUG}$ will be described later in "3. Supplement".

A translation reaction mixture (Table 2) containing 0.04 μM the DNA template, 0.5 mM each of Met, Tyr, and Lys, 50 μM [14C]-Asp, 0.03 μM MetRS, 0.02 μM TyrRS, 0.11 μM LysRS, 0.13 μM AspRS, and 100 μM the N-alkyl-aminoacyl-tRNA$^{Asn-E2}_{GUG}$ was incubated at 37° C. for 60 minutes. The translation product thus obtained was analyzed using tricine-SDS PAGE and autoradiography (Pharox FX, BIO-RAD).

In MALDI-TOF analysis, reaction was made using Asp instead of the above-described [$^{14}$C]-Asp.

The azide group was removed by adding 100 mM TCEP to the translation product and incubating the resulting mixture at 42° C. and pH 8.4 for 30 minutes.

The carboxyl ester group was removed by adding carboxylesterase (Sigma & Aldrich) to the translation product and incubating the resulting mixture at 42° C. and pH 8.4 for 18 hours.

The sample was desalted using C-TIP (Nikkyo Technos), eluted with 80% acetonitrile and 0.5% acetic acid (saturated with CHCA), and analyzed by autoflex II (BRUKER DALTONICS) operated in linear positive mode.

1-2. Streptavidin pull-down of biotinylated peptide/mRNA/cDNA complex for display efficiency analysis Preparation of a TRAP system, a DNA template encoding a peptide, and an N-biotinyl-Phe-tRNA$^{ini}_{CAU}$ will be described later in "3. Supplement".

The DNA template was transcribed and translated into a biotinylated peptide at 37° C. for 25 minutes in a TRAP system (including a 10% v/v PCR reaction mixture containing 0.5 mM each of Tyr, Gly, Ser, and the DNA template, 2.5 µM a puromycin-DNA linker (having a sequence shown in Table S1), 25 µM N-biotinyl-Phe-tRNA$^{ini}_{CAU}$, 1 µM T7 RNA polymerase, and 100 µM any of His, $^{N3C2}$Gly-tRNA$^{Asn-E2}_{GUG}$, and $^{Me}$Glu(OMe)-tRNA$^{Asn-E2}_{GUG}$).

After dissociation from the ribosome by EDTA, a reverse transcription reaction of mRNA was performed using a G5S-4.R20 primer and RNase H-inactivated reverse transcriptase (TOYOBO, Japan). After the reverse transcription reaction was terminated by EDTA and the solution was neutralized with HEPES, the cDNA/mRNA complex that displayed a biotinylated peptide was selectively collected by magnetic beads (VERITAS) coated with streptavidin and was quantitatively determined by quantitative PCR using a T7SD8M2.F44 forward primer and G5S-4.an21.R41 reverse primer.

2. Results

Whether or not a positively charged N-alkyl amino acid was incorporated in a peptide was studied by two steps, that is, a step of ribosomally incorporating, in the peptide, an N-alkylamino acid precursor obtained by protecting a positively-charged amine-containing N-alkyl amino acid with an uncharged azide group and a step of, after translation, deprotecting (Reference Document 40) the resulting product with a trialkylphosphine by a Staudinger reaction to expose the positively-charged amine-containing N-alkyl amino acid (FIG. 1A).

Similarly, whether or not a negatively-charged carboxylic acid-containing N-alkyl amino acid was incorporated in a translation synthesized peptide was studied by translating and thereby synthesizing the peptide using a methyl-esterified carboxylic acid-containing N-alkyl amino acid and exposing the carboxylic acid by using carboxylesterase after the translation (FIG. 1B).

Figure 5:
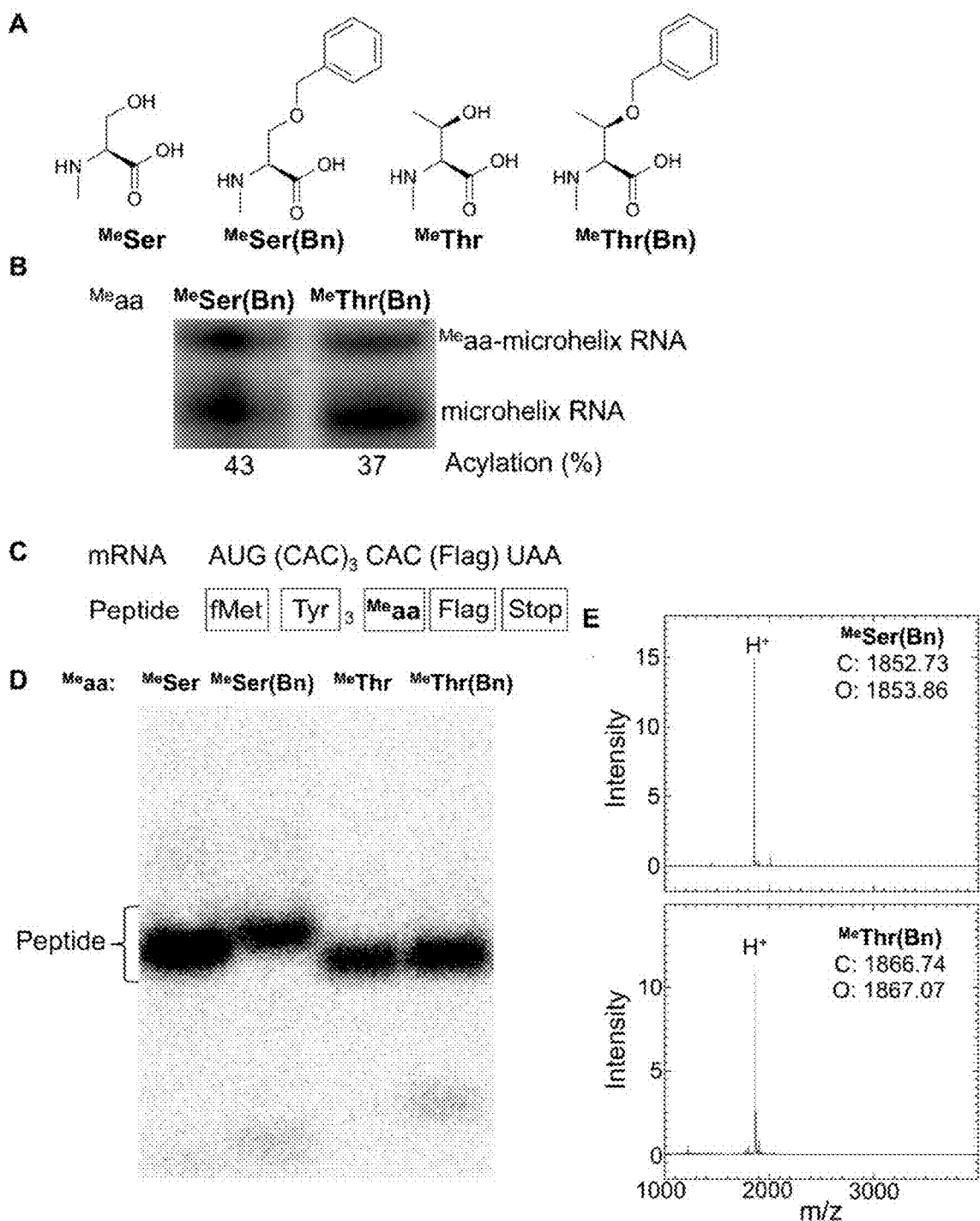
FIG. 5 shows ribosomal synthesis of a peptide containing O-benzyl-N-methyl-serine or O-benzyl-N-methyl-threonine. (A) shows chemical structures of N-methyl-serine ($^{Me}$Ser), O-benzyl-N-methyl-serine [$^{Me}$Ser(Bn)], N-methyl-threonine ($^{Me}$Thr), and O-benzyl-N-methyl-threonine [MeThr(Bn)]. (B) shows confirmation results by acid urea-PAGE of microhelix RNA aminoacylation with the O-benzyl-N-methyl amino acid by dinitro-flexizyme (dFx). DBE corresponding to the O-benzyl-N-methyl amino acid was bound to a microhelix RNA using the dFx. The yields of the N-methyl aminoacyl-($^{Me}$aa-)microhelix RNAs were determined based on the fluorescence intensity of the $^{Me}$aa-microhelix RNAs (I) and the microhelix RNAs (II) using the expression (I)/[(I)+(II)]. (C) shows sequences of mRNA and peptides encoded by the mRNA used for N-methyl amino acid incorporation. (D) shows Tricine-SDS-PAGE of the peptides labeled with [$^{14}$C]-Asp. Peptides were expressed in the presence of the N-methyl aminoacyl-tRNA$^{Asn-E2}_{GUG}$ shown in the drawing and detected by autoradiography. (E) shows MALDI-TOF mass spectra of the O-benzyl-N-methyl amino acid-containing peptides. Calculated value (C:) and observed value (O:) for monovalent ion [M+H]$^+$ are shown in each spectrum.

Further, since the present inventors found that an N-alkyl amino acid having an aromatic side chain became a substrate for ribosomal translation irrespective of its bulk height (Reference Patents 13 and 19) and that N-methylserine and N-methylthreonine modified with a benzyl group were incorporated in a peptide with an efficiency equivalent to that of unmodified N-methylserine and N-methylthreonine (FIG. 5), whether or not a benzyl-esterified carboxylic acid-containing N-alkyl amino acid served as a substrate in translation synthesis and the protecting group could be removed by reacting the translation product with carboxylesterase was studied (FIG. 1B).

Figure 7:
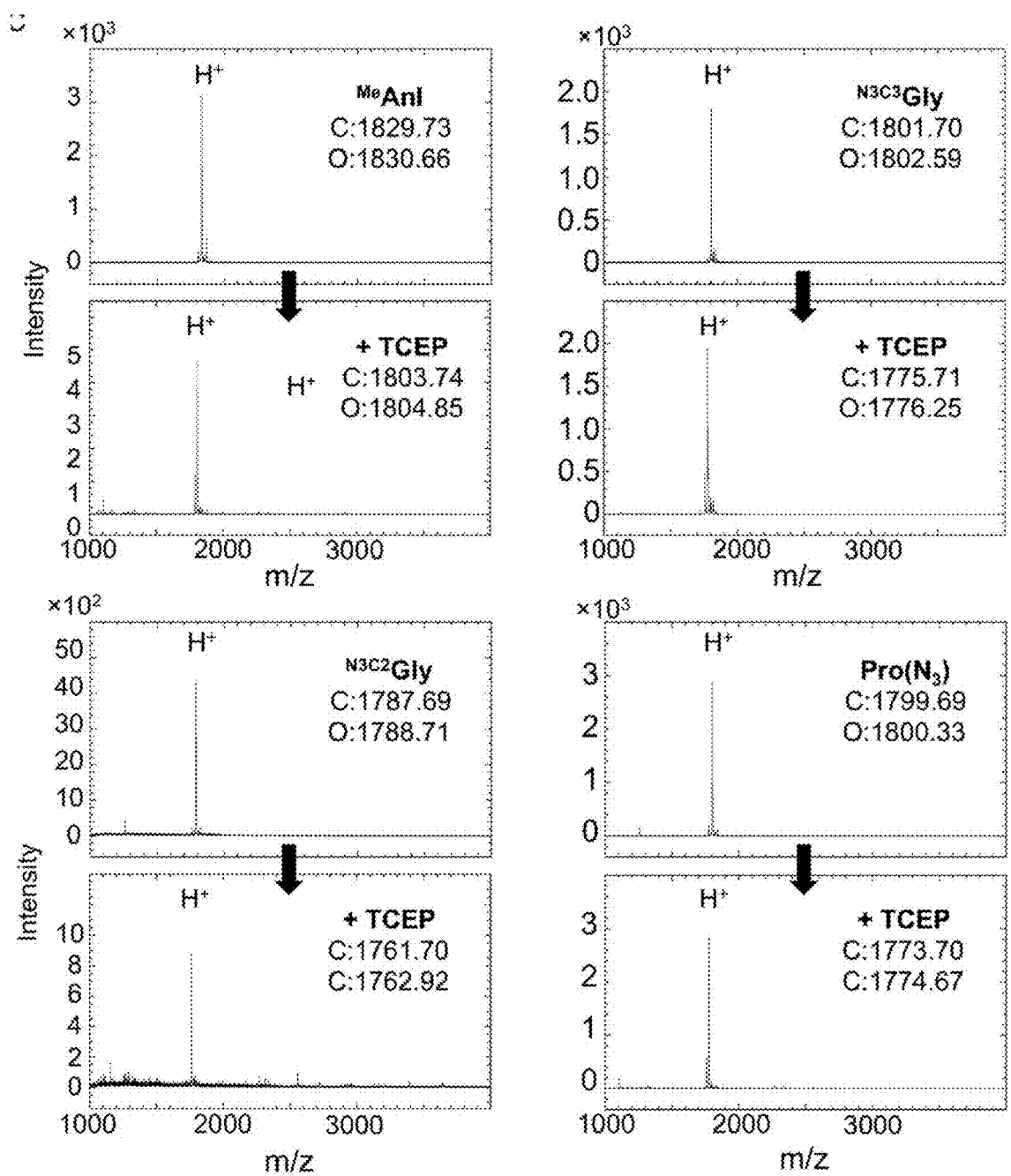
FIG. 7 shows MALDI-TOF mass spectra of peptides containing the azide precursor of an N-alkyl amino acid and a peptide after TCEP treatment shown in FIG. 2C. A calculated value (C:) and an observed value (O:) for a monovalent ion [M+H]$^+$ are shown in each spectrum.

In order to study whether or not an azide-containing N-alkyl amino acid was ribosomally incorporated, first N-methylazide norleucine ($^{Me}$Anl, FIG. 1A) and 3,5-dinitrobenzyl ester (DBE) were chemically synthesized and used as a substrate of artificial tRNA aminoacylated ribozymes (flexizymes) (Reference Documents 41 to 43). It has been confirmed that under aminoacylation conditions optimized using $^{Me}$Anl-DBE and microhelix RNA (tRNA analog), and $^{Me}$Anl, similar to α-N-methyllysine ($^{Me}$Lys), binds to tRNA (FIG. 7).

In order to assess an incorporation efficiency in a ribosome peptide, $^{Me}$Anl and as a control, Lys and $^{Me}$Lys were bound to Asn tRNA (tRNA$^{Asn-E2}$) of Escherichia coli having an anticodon GUG by using flexizyme (Reference Document 44).

Figure 2:
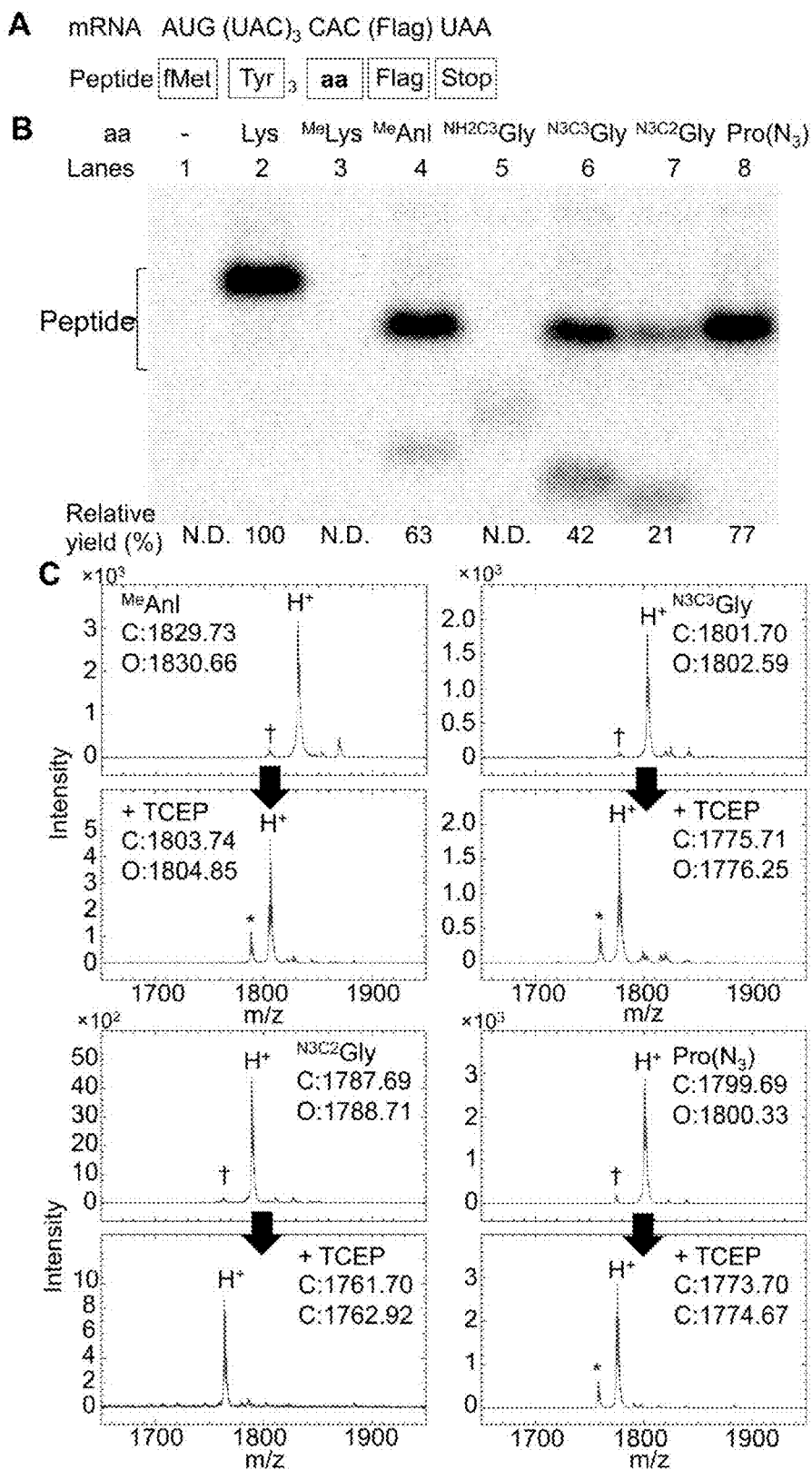
FIG. 2 shows ribosomal synthesis results of a peptide containing a positively charged N-alkyl amino acid by using the method of the present invention. (A) shows the sequence of an mRNA used for incorporation of an N-alkyl amino acid and the sequence of a peptide encoded by the mRNA. (B) shows the tricine-SDS-PAGE analysis results of a peptide labeled with [$^{14}$C]-Asp detected by autoradiography. The peptide was expressed in the presence of non-aminoacyl-tRNA$^{Asn-E2}_{GUG}$ or am inoacyl-tRNA$^{Asn-E2}_{GUG}$ prepared by flexizyme and shown in this drawing. A relative yield of each peptide detected by autoradiography is shown below the gel. Each relative yield is determined by carrying out an experiment twice and finding an average value. (C) shows MALDI-TOF mass spectrum of a translation product (upper panel) and that after TCEP treatment (lower panel). A calculated value (C) of a target peptide and an observed value (O) of a major peak for monovalent ion [M+H]$^+$ are shown. In these spectra, H$^+$ represents a protonated adduct ([M+H]+) of a target peptide; a dagger (†) represents an amine by-product produced during MALDI analysis; and an asterisk (*) shows an unknown minor peak.

Also prepared was a DNA template encoding a peptide having a CAC codon for His for incorporation of an N-alkyl amino acid and having at the C terminal a FLAG tag for isotopic labeling with [$^{14}$C]-Asp (FIG. 2A). A peptide labeled with [$^{14}$C]-Asp was not produced in a His-deficient reconstituted cell-free translation system including the DNA template and non-aminoacylated tRNA$^{Asn-E2}_{GUG}$ (FIG. 2B, Lane 1). Similarly, a peptide was not produced in the presence of $^{Me}$Lys-tRNA$^{Asn-E2}_{GUG}$ (FIG. 2B, Lane 3).

The above finding suggests that similar to the previous report (Reference Document 13), positively charged $^{Me}$Lys is not suited for translation. In a translation system including $^{Me}$Anl-tRNA$^{Asn-E2}_{GUG}$, a peptide in an amount equivalent to that of a peptide produced by proteinogenic Lys-tRNA$^{Asn-E2}_{GUG}$ is expressed (FIG. 2B, Lanes 2 and 4).

This suggests that an incorporation efficiency is improved drastically by masking a charged amine with small neutral azide.

Figure 8:
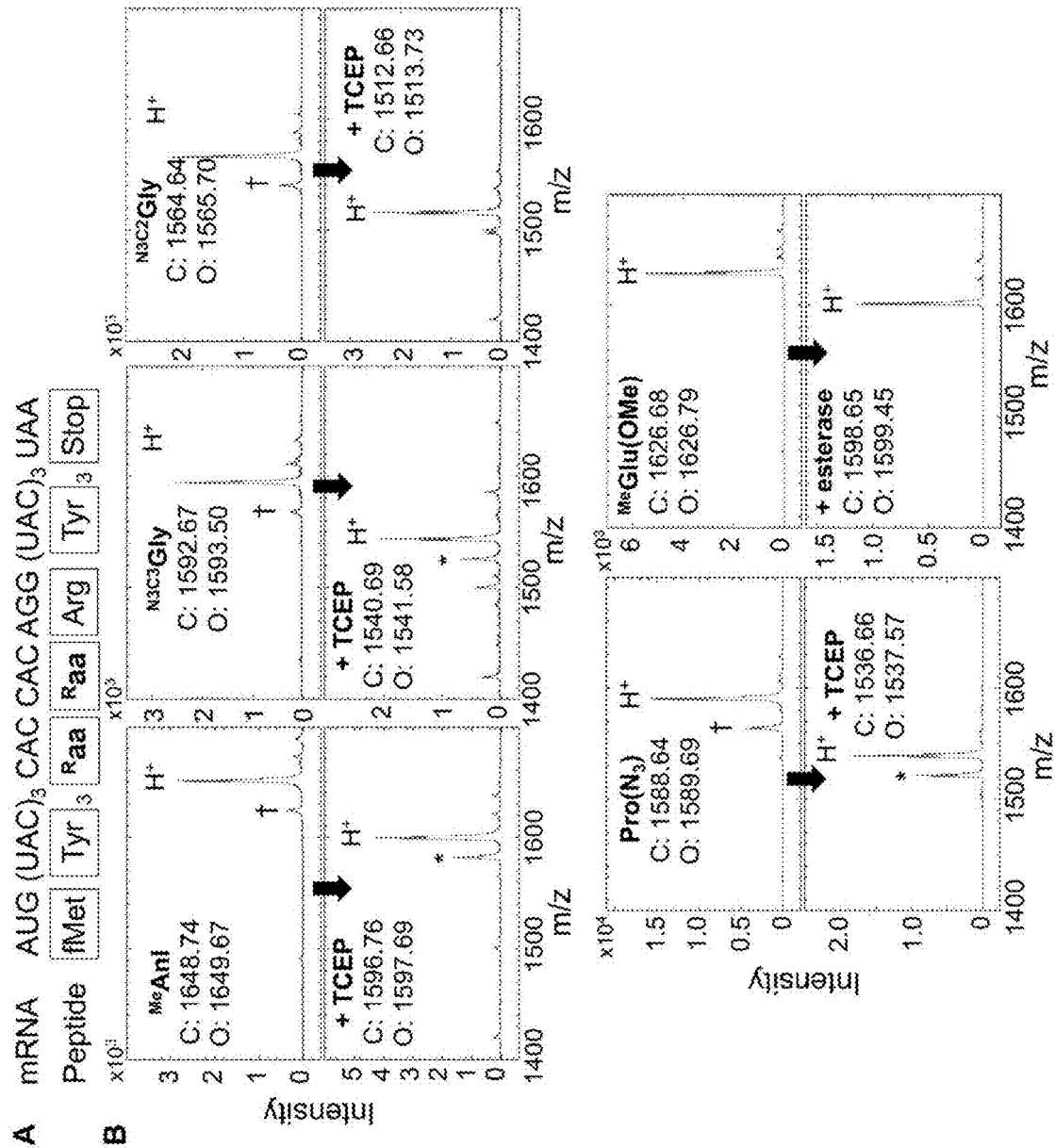
FIG. 8 shows MALDI-TOF mass spectra of peptides obtained by successive double incorporation of N-alkyl amino acids. (A) shows sequences of mRNA and peptides encoded by the mRNA, each used for successive double incorporation of N-alkyl amino acids. A vacant CAC codon is reassigned to N-alkyl amino acids. (B) shows MALDI-TOF mass spectra of the translation products (first and third panels) and those after TCEP- or esterase-treatment (second and forth panels). A calculated value (C:) and an observed value (O:) for monovalent ion [M+H]$^+$ are shown in each spectrum. In these spectra, a dagger (†) represents an amine byproduct produced during MALDI analysis; and an asterisk (*) shows an unknown minor peak.

Incorporation of $^{Me}$Anl was confirmed finally by MALDI-TOF-MS analysis of the desalted translation product (FIG. 2C, 8). The translation product and 100 mM tris(2-carboxyethyl)phosphine (TCEP) were incubated together at 42° C. and pH 8.4 for 0.5 hour to remove the azide group and provide it for MALDI-TOF-MS analysis. The temperature and pH used here were those used in reverse transcription at the time of in vitro peptide selection.

The molecular weight of the main product was equal to that of the desired $^{Me}$Lys-containing peptide (and minor signal of an unknown by-product), from which it has been confirmed that ribosomal incorporation of $^{Me}$Anl and conversion of an azide group into an amino group by a bioorthogonal Staudinger reaction results in ribosomal incorporation of $^{Me}$Lys in a peptide.

Figure 6:
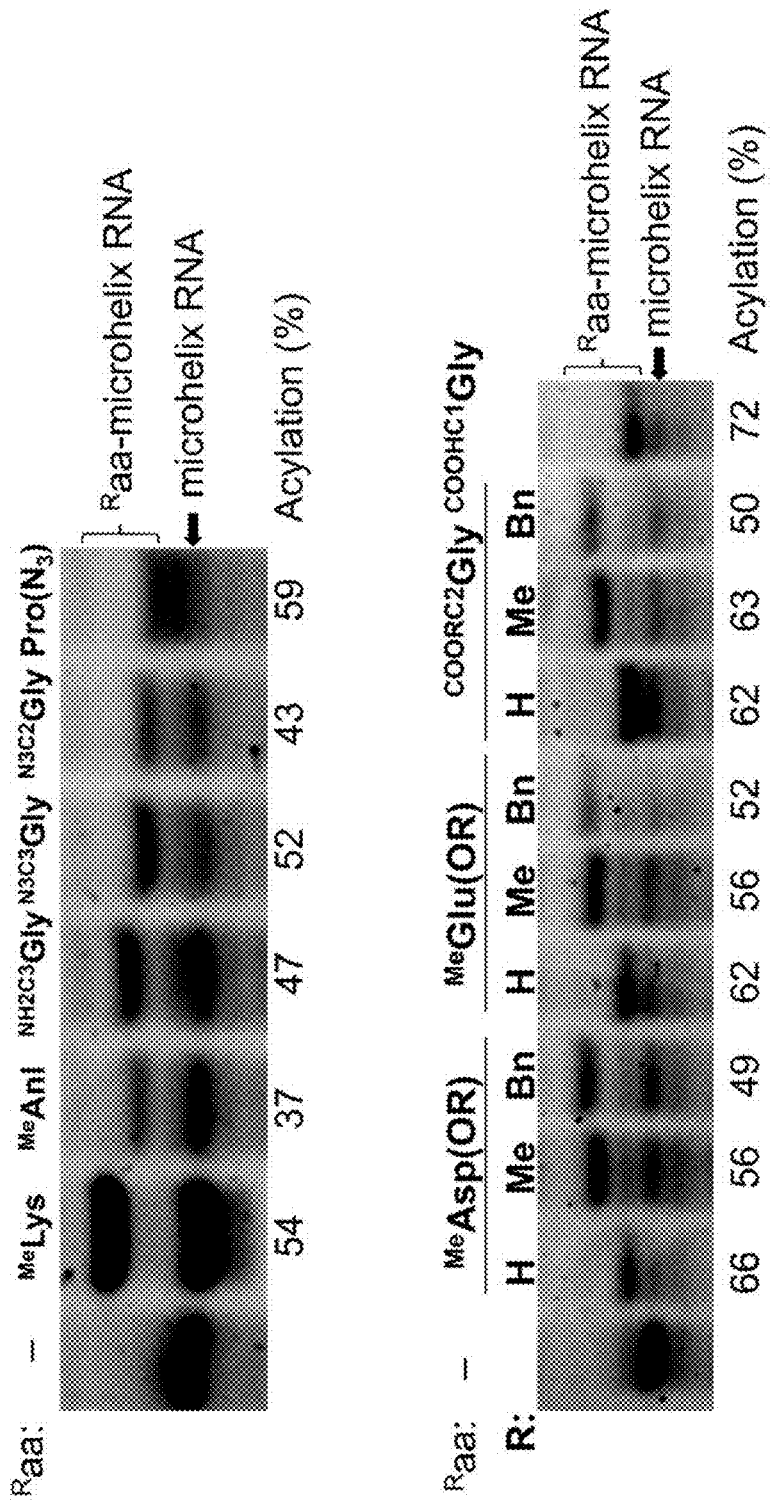
FIG. 6 shows Acid urea-PAGE conformation results of aminoacylation of microhelix RNAs with N-alkyl amino acids by flexizyme (dFx). The yields of the aminoacyl-($^R$aa-) microhelix RNAs were determined based on the fluorescence intensity of the $^R$aa-microhelix RNAs (I) and the microhelix RNAs (II) using the expression (I)/[(I)+(II)].

In order to enlarge an available amino-containing N-alkyl amino acid building block, N-(3-azidopropyl)-glycine ($^{N3C3}$Gly), N-(2-azidoethyl)-glycine ($^{N3C2}$Gly), cis-4-azidoproline [Pro(N3]] (FIG. 1A), and as a control N-(3-aminopropyl)-glycine ($^{NH2C3}$Gly), and respective DBE derivatives corresponding thereto were added to tRNA$^{Asn-E2}$ under optimum conditions by using flexizyme (FIG. 6).

N-(2-Aminoethyl)-glycine ($^{NH2C2}$Gly) and DBE of cis-4-amino-proline [Pro(NH$_2$)] as a negative control did not produce an aminoacylation product, which is presumed to owe to auto-cyclization of an amino acid into a lactam in these aa-DBE and aa-tRNA. In the translation system including $^{N3C3}$Gly-, $^{N3C2}$Gly-, or Pro(N$_3$)-tRNA$^{Asn-E2}_{GUG}$, a peptide labeled with [$^{14}$C]-Asp was expressed (FIG. 2B, Lanes 6 to 8). According to the results of mass analysis, it has been confirmed that $^{N3C3}$Gly, $^{N3C2}$Gly, or Pro(N$_3$) was ribosomally incorporated in the translation product (FIGS. 2C and 7). Then, the azide group was removed as described above. An obvious mass shift corresponding to the peptide containing $^{NH2C3}$Gly, $^{NH2C2}$Gly, or Pro(NH$_2$) was observed. Although a peak of an unknown minor byproduct similar to that observed in TCEP reduction of the $^{Me}$Anl-containing peptide was found from $^{N3C3}$Gly and Pro(N3), homogeneous $^{NH2C3}$Gly-containing peptide was obtained by TCEP reduction of the $^{N3C2}$Gly-containing peptide.

It has already been confirmed that some non-proteinogenic amino acids having a modified skeleton show efficient incorporation in a peptide when they are incorporated singly, but show difficulty in successive plural incorporation (Reference Document 45). Next, fMet-(Tyr)$_3$-($^R$aa)$_2$-Arg-(Tyr)$_3$ ($^R$aa represents an N-alkyl amino acid) was therefore expressed and successive double incorporation of azide-containing N-alkyl amino acids was then tested (FIG. 8A). MALDI-TOF-MS analysis of the desalted translation product has showed that the azide precursors were successively incorporated in the peptide (FIG. 8B). Results of MALDI-TOF-MS analysis of the sample treated with TCEP have showed that a desired product was obtained from all the azide precursors. Similar to FIG. 2C, when a peptide containing $^{N3C2}$Gly- was used, the N-alkyl amino acid incorporated in the peptide was most uniformly positively charged.

Next, in order to study whether or not an N-alkyl amino acid containing an esterified carboxylic acid was ribosomally incorporated, DBEs of chemically synthesized N-methylaspartic acid O-methyl ester and O-benzyl ester (FIG. 1B, $^{Me}$Asp(OMe) and $^{Me}$Asp(OBn) were synthesized. It has been confirmed that similar to N-methylaspartic acid ($^{Me}$Asp), either ester binds to tRNA (FIG. 6).

The translation assay using a translation system to which $^{Me}$Asp(OBn)-tRNA$^{Asn-E2}{}_{GUG}$ has been added instead of His has showed that similar to the previous experiment results (Reference Document 13), negatively-charged $^{Me}$Asp is not introduced in a peptide (FIG. 2B, Lane 2).

In the translation system including $^{Me}$Asp(OMe)-tRNA$^{Asn-E2}{}_{GUG}$ or $^{Me}$Asp(OBn)-tRNA$^{Asn-E2}{}_{GUG}$, on the other hand, a peptide in an amount equivalent to that of a peptide containing proteinogenic Glu-tRNA$^{Asn-E2}{}_{GUG}$ is expressed (FIG. 2B, comparison between Lane 1 and Lane 3 or 4). This suggests that a carboxylic acid methyl ester or benzyl ester markedly increases an incorporation efficiency. Mass analysis of a desalted translation product however revealed that any peptide mainly contained not intended $^{Me}$Asp(OMe) or $^{Me}$Asp(OBn) but aspartimide. It is presumed that $^{Me}$Asp(OMe) or $^{Me}$Asp(OBn) is incorporated smoothly during translation but as can often be found in solid phase synthesis of a peptide using Fmoc, aspartimide may be formed as a result of ring-closure of a p carboxyl ester and an amide skeleton. The aspartimide formation is presumed to occur during mass analysis because a peptide containing $^{Me}$Asp can be detected at the time of hydrolysis with carboxylesterase.

Next, an N-alkyl amino acid containing another esterified carboxylic acid and ribosomally incorporated in a peptide was searched (FIG. 1B).

tRNA$^{Asn-E2}$s to which N-methylglutamic acid O-methyl ester and O-benzyl ester and N-(2-carboxyethyl)-glycine O-methyl ester and O-benzyl ester (FIG. 1B, $^{Me}$Glu(OMe), $^{Me}$Glu(OBn), $^{COOMeC2}$Gly, and $^{COOBnC2}$Gly) had been bound were prepared under optimum conditions by using DBEs corresponding thereto and flexizyme (FIG. 6).

Figure 3:
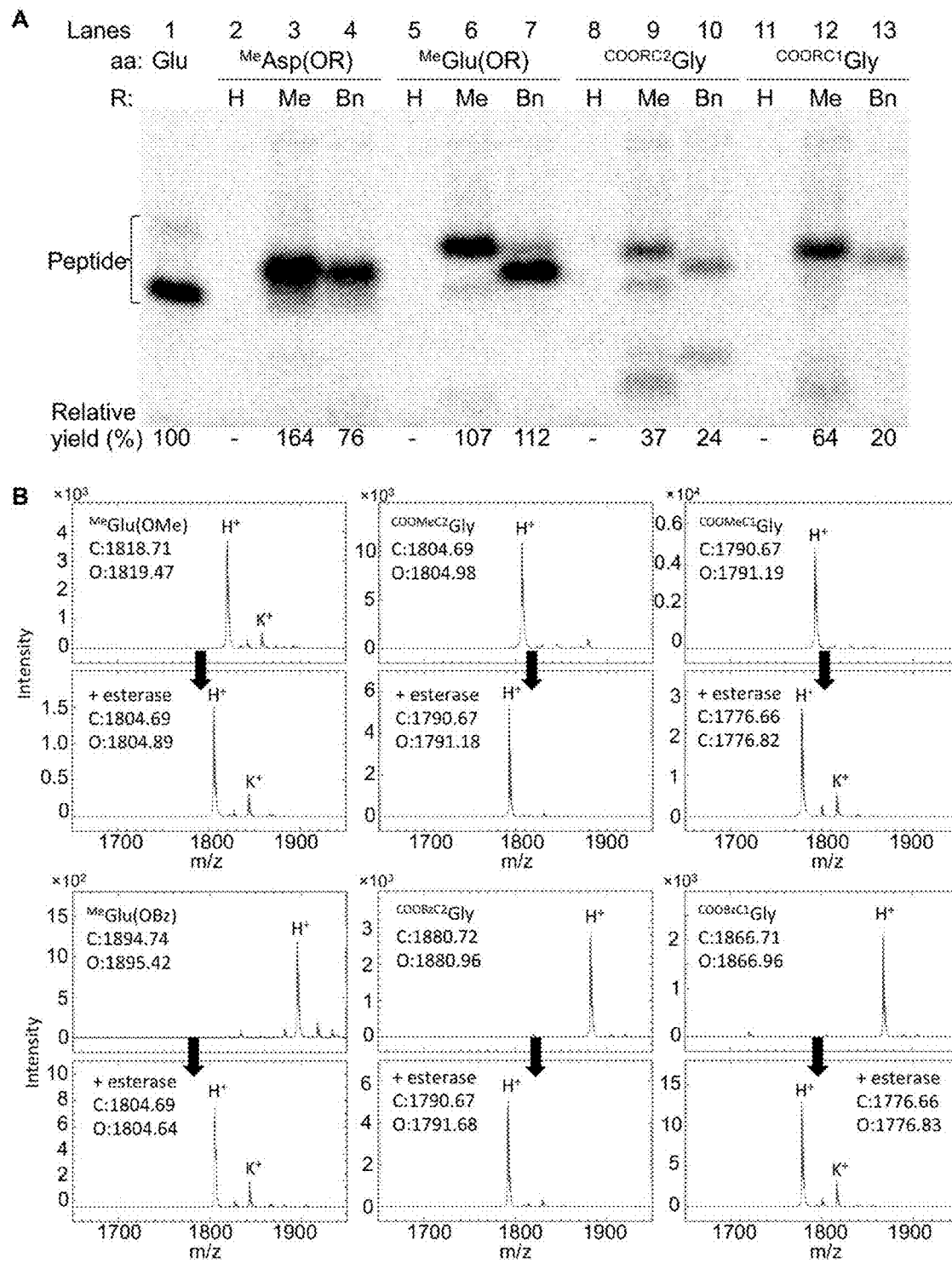
FIG. 3 shows ribosomal synthesis results of a peptide containing a negatively-charged N-alkyl amino acid by the method of the present invention. (A) shows tricine-SDS-PAGE analysis results of a peptide labeled with [$^{14}$C]-Asp detected by autoradiography. The peptide was expressed in the presence of aminoacyl-tRNA$^{Asn-E2}_{GUG}$ prepared by flexizyme. A relative yield of each peptide detected by autoradiography is shown below the gel. Each relative yield is determined by carrying out an experiment twice and finding an average value. (B) shows a MALDI-TOF mass spectrum of translation products (first and third panels) and that after carboxyl esterase treatment (second and fourth panels). A calculated value (C) of a target peptide and an observed value (O) of a major peak for monovalent ion [M+H]$^+$ are shown. In these spectra, H$^+$ represents a protonated adduct ([M+H]$^+$) of a target peptide; and K$^+$ represents a potassium adduct ([M+K]$^+$) thereof
Figure 9:
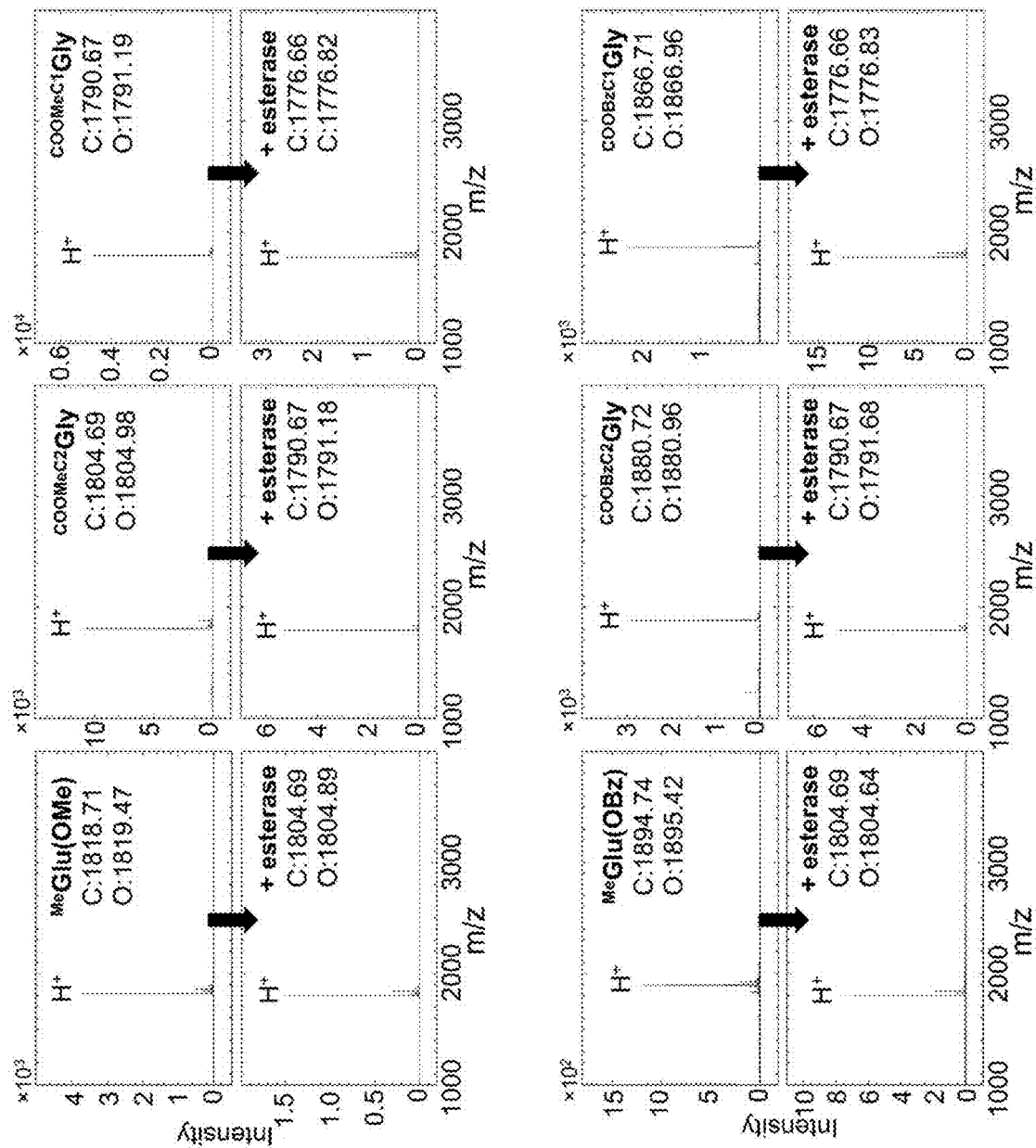
FIG. 9 shows MALDI-TOF mass spectra of peptides containing an ester precursor of an N-alkyl amino acid and peptides after carboxylesterase treatment shown in FIG. 2C. A calculated value (C:) and an observed value (O:) for monovalent ion [M+H]$^+$ are shown in each spectrum.

As a result of analysis of the aminoacylation of N-carboxymethyl-glycine O-methyl ester and O-benzyl ester (FIG. 1B, $^{COOMeC1}$Gly and $^{COOBnC1}$Gly), a main band corresponded to N-carboxymethyl-glycyl-RNA and the band of an intended esterified N-carboxymethyl-RNA was observed only slightly. This is presumed to be caused by hydrolysis of the side-chain α-carboxyl ester (no data) at the time of aminoacylation. The aminoacylation time was therefore optimized by direct translation assay of $^{COOMeC1}$Gly and $^{COOBnC1}$Gly and it has been found that a [$^{14}$C]-Asp-labeled peptide was obtained by aminoacylation for 18 hours. Similarly, it has been confirmed that $^{Me}$Glu(OMe), $^{Me}$Glu(OBn), $^{COOMeC2}$Gly, and $^{COOBnC2}$Gly were incorporated in a peptide (FIG. 3B, Lanes 6, 7, 9, 10, 12, and 13) were incorporated in a peptide but none of negatively charged $^{Me}$Glu, $^{COOHC2}$Gly, and $^{COOHC1}$Gly were incorporated (FIG. 3B, Lanes 5, 8, and 11). It has been confirmed by mass analysis of the peptides thus expressed that with respect to all the amino acids provided for the test, esterified carboxylic-acid-containing N-alkyl amino acid was incorporated (FIGS. 3C and 9).

Next, in order to show conversion of an ester into a corresponding carboxylic acid under mild conditions, the translation product was treated with commercially available carboxylesterase at 42° C. and pH 8.4 for 18 hours without being purified. It has been confirmed from the MALDI-TOF-MS spectrum of samples treated with esterase, the ester group of all the amino acids was quantitatively converted into a carboxylic acid and a carboxylic acid-containing N-alkyl amino acid was exposed (FIGS. 3C and 9).

Further, it has been confirmed by MALDI-TOF-MS that in addition to efficient single incorporation of $^{Me}$Glu(OMe), two $^{Me}$Glu(OMe)s were incorporated successively and at the same time, deprotected with carboxylesterase (FIG. 8).

Figure 4:
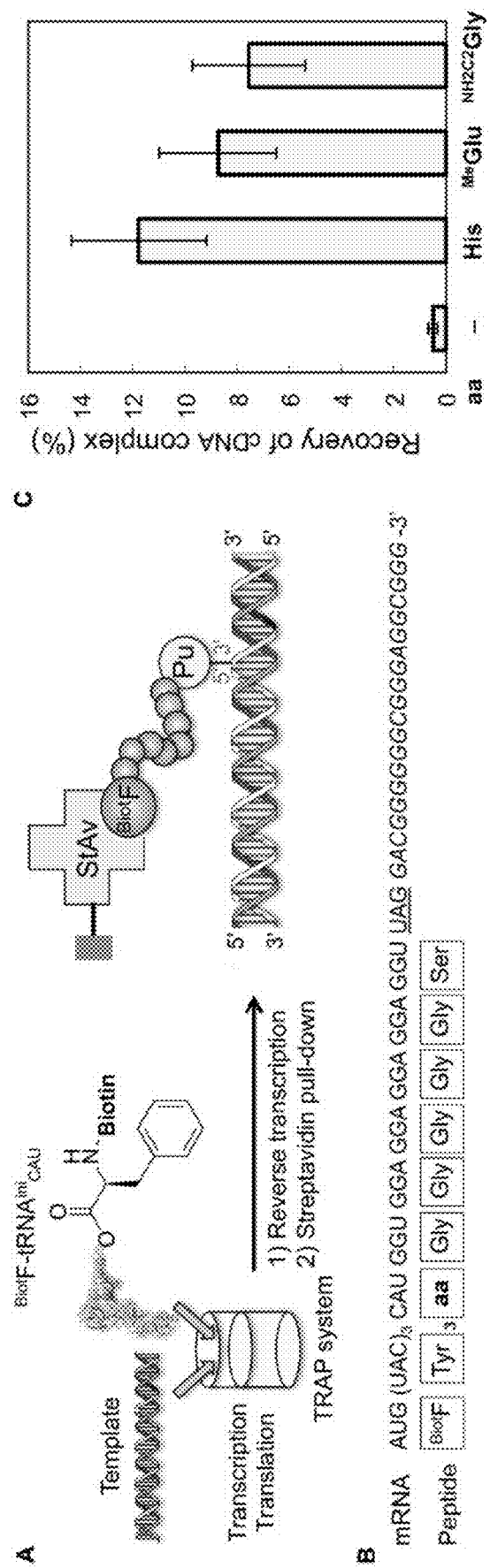
FIG. 4 shows suitability of charged N-alkyl amino acid incorporation by the present invention to TRP display. (a) shows the outline of streptavidin pull-down of biotin-labeled peptide displayed on its mRNA-cDNA complexes to evaluate peptide display efficiency. In the TRAP system, an expressed peptide is spontaneously displayed on mRNA encoding itself via a puromycin-DNA linker in the translation system. An mRNA displaying a peptide containing N-biotinyl-phenylalanine ($^{Biot}$F) was separated from an mRNA not displaying a peptide by using streptavidin (StAv)-immobilized beads and quantitatively determined by quantitative PCR. (b) shows the mRNA used for determination of a display efficiency and a sequence of the peptide. An initiator AUG codon is reassigned to $^{Bio}$F. An empty UAG codon for stopping ribosome and efficiently transferring the peptide to puromycin is underlined; a binding region of a puromycin DNA linker is shown in italics; and aa represents a charged N-alkyl amino acid or histidine as a control. (c) shows a display efficiency of the proteinogenic peptide as a control and a peptide containing charged N-alkyl amino acid.

In the end, suitability of incorporation of a charged N-alkyl amino acid via deprotection after translation for in vitro TRAP (Transcription-translation coupled with Association of Puromycin-linker) display developed by the present inventors was studied (FIG. 4A). In TRAP display, puromycin was bound to the 3' end of mRNA and 3' end of a complementary oligo DNA linker and the puromycin-bound product was directly added to a cell-free transcription-translation system (FIG. 4A). In this system (TRAP system), DNAs were successively transcribed and translated into peptides and the peptides are spontaneously displayed (trapped) on an mRNA encoding the peptides themselves via a puromycin linker. Thus, the peptide-mRNA complex is made from a template DNA corresponding thereto in the TRAP system.

Display efficiency of a peptide containing a charged N-alkyl amino acid was evaluated by constructing DNA encoding an fMet-(Tyr)$_3$-aa-(Gly)$_5$-Ser peptide (FIG. 4B). N-Biotinyl-Phe ($^{Biot}$F) was bound to tRNA$^{ini}{}_{CAU}$ and it was used for labelling the peptide with the biotin at the N terminal of the peptide (FIG. 4a). His, $^{N3C2}$Gly-tRNA$^{Asn-E2}{}_{GUG}$, or $^{Me}$Glu(OMe)-tRNA$^{Asn-E2}{}_{GUG}$ was added to a TRAP system including the template DNA and $^{Biot}$F-tRNA$^{ini}{}_{GUG}$.

It has been confirmed that the biotinylated peptide containing a charged N-alkyl amino acid ($^{Me}$Glu or $^{NH2C2}$Gly) is displayed on the mRNA with an efficiency equivalent to that of a proteinogenic peptide of a control as a result of streptavidin pull-down of the translation product containing $^{N3C2}$Gly-tRNA$^{Asn-E2}{}_{GUG}$ or $^{Me}$Glu(OMe)-tRNA$^{Asn-E2}{}_{GUG}$ and deprotection therefrom with TCEP or carboxylesterase (FIG. 4C).

In the streptavidin pull-down experiment of the translation product of a control containing non-aminoacylated tRNA$^{Asn-E2}{}_{GUG}$, the biotinylated peptide was not displayed on mRNA (FIG. 4C).

3. Complement 3-1. Synthesis of N-Alkyl Amino Acid 3,5-Dinitrobenzyl Ester

All N-alkyl amino acids, boc-protected N-alkyl amino acid, and Fmoc-protected N-alkyl amino acid were purchased from Watanabe Chemical, TCI, Chem-Impex, or Apollo Scientific. An azide-containing N-alkyl amino acid was synthesized using a primary amine-containing N-alkyl amino acid corresponding thereto by the method of Reference Document 46. All N-alkyl amino acids were converted into 3,5-dinitrobenzyl esters (DBEs) by the method of Reference Documents 13, 41, and 19. An N-alkyl amino acid DBE was methyl esterified with trimethylsilyldiazomethane. An N-alkyl amino acid DBE was benzyl esterified with benzyl bromide in a manner similar to 3,5-dinitrobenzyl esterification of an amino acid (Reference Document 41).

3-2. Aminoacylation assay of microhelix RNA and N-alkyl amino acid by flexizyme

Microhelix RNA and dinitroflexizyme (dFx) were prepared by run-off transcription of an appropriate template (Reference Document 41). An aminoacylation efficiency was measured using the microhelix RNA. A reaction was usually performed under the following condition: 5 µL of 25 µM dFx, 25 µM microhelix RNA, and 5 mM N-alkyl amino acid DBE (in 0.1 M Hepes-K buffer having pH 7.5), and 20 mM $MgCl_2$ and 20% DMSO (on ice).

The measurement was performed in the following order: 50 µM microhelix RNA (in 0.2 M Hepes-K buffer having pH 7.5 (2.5 µL)) was heated at 95° C. for one minute and then cooled to room temperature for 5 minutes. To the resulting mixture were added $MgCl_2$ (100 mM, 1 µL) and dFx (250 µM, 0.5 µL). Then, an N-alkyl amino acid DBE (in DMSO, 25 mM, 1 µL) was added to initiate the reaction, followed by incubation on ice. The reaction was then terminated with 15 µL of a loading buffer (150 mM sodium acetate, pH 5, 10 mM EDTA, and 83% formamide). The resulting sample was analyzed with 20% denaturing acid PAGE (50 mM sodium acetate having pH 5, 6M urea). The RNA was stained with etidium bromide and analyzed using Pharos FX (BIO-RAD).

3-3. Preparation of $tRNA^{Asn-E2}$ Aminoacylated with N-Alkyl Amino Acid by Flexizyme $tRNA^{Asn-E2}$ was prepared through run-off transcription of an appropriate template by the method of Reference Documents 19 and 44. The aminoacylation of the $tRNA^{Asn-E2}$ was usually performed under the following conditions: 50 µL of 25 µM dFx, 25 µM $tRNA^{Asn-E2}$, and 5 mM N-alkyl amino acid DBE (in 0.1 M Hepes-K buffer having pH 7.5), 20 mM $MgCl_2$, and 20% DMSO (on ice).

The following is the procedure: 50 µM $tRNA^{Asn-E2}$ (in 0.2 M Hepes-K buffer having pH 7.5 (25 µL)) was heated at 95° C. for one minute and then cooled to room temperature over 5 minutes. To the resulting mixture were added $MgCl_2$ (100 mM, 10 µL) and dFx (250 µM, 5 µL). Then, an N-alkyl amino acid DBE (in DMSO, 25 mM, 10 µL) was added to initiate the reaction, followed by incubation on ice. The reaction was then terminated with 150 µL of 0.6 mM sodium acetate having pH 5. The RNA was recovered by ethanol precipitation and rinsed with 70% ethanol.

3-4. Preparation of Template DNA Encoding Peptide

Primers used for preparation of the template DNA are shown in Table 1. A template DNA encoding the peptide shown in FIG. 2A was prepared using a forward primer T7pEpsSD6MY3.F37 and a reverse primer eSD6MY3HFlag.R40 for primer extension and a forward primer T7pEpsSD6.F40 and a reverse primer Flaguaa.R33 for amplification. A template DNA encoding the peptide shown in FIG. 8A was prepared using a forward primer T7pEpsSD6MY3.F37 and a reverse primer eSD6MY3H2RY3.R40 for primer extension and a forward primer T7pEpsSD6.F40 and a reverse primer RY3uaa2.R18 for amplification. A template DNA encoding the peptide shown in FIG. 4B was prepared using a forward primer SD8M2-Y3H-G5S-4.F40 and a reverse primer G5S-4.an21.R41 for primer extension and Taq DNA polymerase (Genscript) for annealing and extension. Then, the dsDNA thus obtained was amplified using Taq DNA polymerase while using a forward primer T7SD8M2.F44, a reverse primer G5S-4.an21.R41.

3-5. Preparation of Reconstituted Cell-Free Translation System

The reconstituted translation system was prepared in accordance with the previous reports (Reference Documents 22, 20, 16, and 45). The concentration of each of the protein factor and ribosome in the translation reaction mixture is shown in Table 2. The concentration of each of the tRNA and the low molecular compound in the translation reaction mixture is shown in Table 3.

3-6. Preparation of TRAP System

The TRAP system was prepared in the above-mentioned translation system including 2.5 µM puromycin linker (BEX, Japan) and 1 µM T7 RNA polymerase.

3-7. Preparation of N-Biotinyl-Phe-$tRNA^{fMet}_{CAU}$

Enhanced flexizyme (eFx) and $tRNA^{fMet}tCAU$ were prepared through run-off transcription of an appropriate template in accordance with Reference Documents 41 and 47. N-Biotinyl-Phe-CME was prepared in accordance with Reference Document 48. Aminoacylation of $tRNA^{fMet}_{CAU}$ was performed under the following conditions: 50 µL of 25 µM eFx, 25 µM $tRNA^{fMet}_{CAU}$, and 5 mM N-biotinyl-Phe-CME (in 0.1 M Hepes-K buffer having pH 8), 600 mM MgCl2, and 20% DMSO (on ice). The following was the procedure: 50 µM $tRNA^{fMet}_{CAU}$ (in 0.2 M Hepes-K buffer having pH 7.5 (25 µL)) was heated at 95° C. for one minute and then cooled to room temperature over 5 minutes. To the resulting mixture were added $MgCl_2$ (3 M, 10 µL) and eFx (250 µM, 5 µL). Then, N-biotinyl-Phe-CME (in DMSO, 25 mM, 10 µL) was added to initiate the reaction, followed by incubation on ice. The reaction was then terminated with 150 µL of 0.6 mM sodium acetate having pH 5. The RNA was recovered by ethanol precipitation and rinsed twice with 70% ethanol containing 0.1 M sodium acetate (pH 5) and once with 70% ethanol.

3-8. Ribosomal Synthesis of Peptide Containing Two Successive N-Alkyl Amino Acids A reaction mixture containing 0.04 µM DNA template, 0.5 mM each of Met, Tyr, and Arg, 0.03 µM MetRS, 0.02 µM TyrRS, 0.03 µM ArgRS, and 100 µM N-alkylaminoacyl-$tRNA^{Asn-E2}_{GUG}$ was incubated at 37° C. for 60 minutes. For MALDI-TOF MS analysis, the translation product was desalted with C-TIP (Nikkyo Technos), eluted with 80% acetonitrile and 0.5% acetic acid (saturated with CHCA), and analyzed in a linear positive mode of autoflexII (BRUKER DALTONICS).

Oligo DNAs used for reverse transcription reaction, TRAP display method, or preparation of template DNA encoding a peptide (purchased from Greiner Bio-One or BEX)

TABLE 1

| Names | Sequences | Sequence ID NOS |
|---|---|---|
| T7pEpsSD6MY3.F37 | GGT TAACT TTAAC AAGGA GAAAA AC ATG TAC TAC TAC | 1 |
| eSD6MY3HFlag.R40 | GTCGTCGTCCTTGTAGTC GTG GTAGTAGTACATGTTTTT | 2 |
| T7pEpsSD6.F40 | GGCGT AATAC GACTC ACTAT AGGGT TAACT TTAAC AAGGA | 3 |
| Flaguaa.R33 | CGAAGC TTA CTT GTC GTC GTC GTC CTT GTA GTC | 4 |

TABLE 1-continued

| Names | Sequences | Sequence ID NOS |
|---|---|---|
| eSD6MY3H2RY3.R40 | TTAGTAGTAGTACCT GTGGTG GTAGTAGTACATGTTTTT | 5 |
| RY3uaa2.R18 | TTATTAGTAGTAGTACCT | 6 |
| SD8M2-Y3H-G5S-4.F40 | AGGTGATATTT ATG TAC TAC TAC CAT GGT GGA GGA GGA GG | 7 |
| G5S-4.an21.R41 | CCCGCCTCCCGCCCCCGTC CTA GCT ACC TCC TCC TCC ACC | 8 |
| T7SD8M2.F44 | ATACTAATACGACTCACTAT AGGATTAAGGAGGTGATATT TATG | 9 |
| G5S-4.R20 | TAGCT ACCTC CTCCT | 10 |
| Puromycin-DNA linker | CCACC CCCGC CTCCC GCCCC CCGTC C-(SPC18)$_5$-CC-Puromycin | 11 |

SPC18: 18-O-Dimethoxytritylhexaethyleneglycol,1-[(2-cyanoethyl)-(N,N-diisopropyl)]-phosphoramidite Concentration of protein component and ribosome in translation mixture solution. Creatine kinase and Myokinase were purchased from Roche Diagnostics and Sigma-Aldrich, respectively.

TABLE 2

| Name | Concentration (μM) |
|---|---|
| MTF | 0.6 |
| IF1 | 2.7 |
| IF2 | 0.4 |
| IF3 | 1.5 |
| EF-G | 0.26 |
| EF-Tu | 10 |
| EF-Ts | 10 |
| RF2 | 0.25 |
| RF3 | 0.17 |
| RRF | 0.5 |
| Nucleoside-diphosphate kinase | 0.1 |
| Inorganic pyrophosphatase | 0.1 |
| T7 RNA polymerase | 0.1 |
| Creatine kinase | 4 (μg/mL) |
| Myokinase | 3 (μg/mL) |
| Ribosome | 1.2 |

Concentration of low molecular compound and tRNA in translation mixture solution. Creatine phosphate and *E. coli* total tRNA were purchased from Roche Diagnostics, while 10-formyl-5,6,7,8 tetrahydrofolic acid was synthesized.

TABLE 3

| Name | Concentration (mM) |
|---|---|
| ATP | 2 |
| GTP | 2 |
| CTP | 1 |
| UTP | 1 |
| Creatine phosphate | 20 |
| Hepes-KOH pH 7.6 | 50 |
| Potassium acetate | 100 |
| Magnesium acetate | 12 |
| Spermidine | 2 |
| DTT | 1 |

TABLE 3-continued

| Name | Concentration (mM) |
|---|---|
| 10-formyl-5,6,7,8 tetrahydrofolic acid | 0.1 |
| *E. coil* total tRNAs | 1.5 (mg/mL) |

REFERENCE DOCUMENTS

1. Yamagishi, Y. et al. Chem. Biol. 18, 1562-1570 (2011).
2. Baeriswyl, V. & Heinis, C. Protein Eng. Des. Sel. 26, 81-89 (2013).
3. Kwon, Y. U. & Kodadek, T. J. Am. Chem. Soc. 129, 1508-1509 (2007).
4. Tan, N.C., Yu, P., Kwon, Y. U. & Kodadek, T. Bioorg. Med. Chem. 16, 5853-5861 (2008).
5. Mattheakis, L. C., Bhatt, R. R. & Dower, W. J. Proc. Natl. Acad. Sci. USA 91, 9022-9026 (1994).
6. Hanes, J. & Pluckthun, A. Proc. Natl. Acad. Sci. USA 94, 4937-4942 (1997).
7. Nemoto, N., MiyamotoSato, E., Husimi, Y. & Yanagawa, H. FEBS Lett. 414, 405-408 (1997).
8. Roberts, R. W. & Szostak, J. W. Proc. Natl. Acad. Sci. USA 94, 12297-12302 (1997).
9. Merryman, C. & Green, R. Chem. Biol. 11, 575-582 (2004).
10. Tan, Z., Forster, A. C., Blacklow, S. C. & Cornish, V. W. J. Am. Chem. Soc. 126, 12752-12753 (2004).
11. Hartman, M. C., Josephson, K., Lin, C. W. & Szostak, J. W. PLoS One 2, e972 (2007).
12. Zhang, B. et al. J. Am. Chem. Soc. 129, 11316-11317 (2007).
13. Kawakami, T., Murakami, H. & Suga, H. Chem. Biol. 15, 32-42 (2008).
14. Sando, S., Masu, H., Furutani, C. & Aoyama, Y. Org Biomol Chem 6, 2666-2668 (2008).
15. Subtelny, A. O., Hartman, M. C. & Szostak, J. W. J. Am. Chem. Soc. 130, 6131-6136 (2008).
16. Kawakami, T. et al. Nat. Chem. Biol. 5, 888-890 (2009).
17. Pavlov, M. Y. et al. Proc. Natl. Acad. Sci. USA 106, 50-54 (2009).
18. Subtelny, A. O., Hartman, M. C. & Szostak, J. W. Angew. Chem. Int. Ed. 50, 3164-3167 (2012).
19. Kawakami, T., Murakami, H. & Suga, H. J. Am. Chem. Soc. 130, 16861-16863 (2008).
20. Josephson, K., Hartman, M. C. T. & Szostak, J. W. J. Am. Chem. Soc. 127, 11727-11735 (2005).
21. Forster, A. C., Weissbach, H. & Blacklow, S. C. Anal. Biochem. 297, 60-70 (2001).
22. Shimizu, Y. et al. Nat. Biotechnol. 19, 751-755 (2001).
23. Karginov, V. A. et al. J. Am. Chem. Soc. 119, 8166-8176 (1997).
24. Short, G. F., 3rd et al. Biochemistry 39, 8768-8781 (2000).
25. Choudhury, A. K., Golovine, S. Y., Dedkova, L. M. & Hecht, S. M. Biochemistry 46, 4066-4076 (2007).
26. Bain, J. D., Wacker, D. A., Kuo, E. E. & Chamberlin, A. R. Tetrahedron 47, 2389-2400 (1991).
27. Ellman, J. A., Mendel, D. & Schultz, P. G. Science 255, 197-200 (1992).
28. Chung, H. H., Benson, D. R., Cornish, V. W. & Schultz, P. G. Proc. Natl. Acad. Sci. USA 90, 10145-10149 (1993).
29. Chung, H. H., Benson, D. R. & Schultz, P. G. Science 259, 806-809 (1993).
30. Kawakami, T. & Murakami, H. J. Nucleic Acids 2012, 713510 (2012).

31. Schlippe, Y. V., Hartman, M. C., Josephson, K. & Szostak, J. W. J. Am. Chem. Soc. 134, 10469-10477 (2012).
32. Seebeck, F. P. & Szostak, J. W. J Am Chem Soc 128, 7150-7151 (2006).
33. Wang, J., Schiller, S. M. & Schultz, P. G. Angew. Chem. Int. Ed. 46, 6849-6851 (2007).
34. Guo, J., Wang, J., Lee, J. S. & Schultz, P. G. Angew. Chem. Int. Ed. 47, 6399-6401 (2008).
35. Goto, Y., Iwasaki, K., Torikai, K., Murakami, H. & Suga, H. Chem. Commun., 3419-3421 (2009).
36. Seebeck, F. P., Ricardo, A. & Szostak, J. W. Chem. Commun. 47, 6141-6143 (2011).
37. Hofmann, F. T., Szostak, J. W. & Seebeck, F. P. J. Am. Chem. Soc. 134, 8038-8041 (2012).
38. Wang, Z. U. et al. Biochemistry 51, 5232-5234 (2012).
39. Nakajima, E., Goto, Y., Sako, Y., Murakami, H. & Suga, H. ChemBioChem 10, 1186-1192 (2009).
40. Kohn, M. & Breinbauer, R. Angew. Chem. Int. Ed. 43, 3106-3116 (2004).
41. Murakami, H., Ohta, A., Ashigai, H. & Suga, H. Nat. Methods 3, 357-359 (2006).
42. Ohuchi, M., Murakami, H. & Suga, H. Curr. Opin. Chem. Biol. 11, 537-542 (2007).
43. Xiao, H., Murakami, H., Suga, H. & Ferre-D'Amare, A. R. Nature 454, 358-361 (2008).
44. Ohta, A., Murakami, H., Higashimura, E. & Suga, H. Chem. Biol. 14, 1315-1322 (2007).
45. Fujino, T., Goto, Y., Suga, H. & Murakami, H. J. Am. Chem. Soc. 135, 1830-1837 (2013).
46. A. J. Link, M. K. Vink, and D. A. Tirrell, Nature Protocols 2 (8), 1879-1883 (2007).
47. Yuki Goto, Atsushi Ohta, Yusuke Sako et al., ACS Chem. Biol. 3 (2), 120-129 (2008).
48. H. Saito, D. Kourouklis, and H. Suga, EMBO J. 20 (7), 1797-1806 (2001).

SEQUENCE LISTING FREE TEXT

Sequence ID NOS: 1 to 10 represent the sequence of a primer.
Sequence ID NO: 11 represents the sequence of a puromycin DNA linker.

What is claimed is:

1. A cell-free translation system for producing a charged non-proteinogenic amino acid-containing peptide or a peptide library thereof, comprising:
   (i) at least one tRNA having bound thereto a non-proteinogenic amino acid having in its side-chain a charged group masked by a protecting group; and
   (ii)(a) a nucleic acid that encodes the peptide and contains at least one codon corresponding to an anticodon of the tRNA, or (b) a nucleic acid library that encodes the peptide library, each nucleic acid containing at least one codon corresponding to an anticodon of the tRNA;
   wherein the charged group is an amino group and the combination of the charged group and the protecting group is an azide group.

2. A cell-free translation system for producing a charged non-proteinogenic amino acid-containing peptide or a peptide library thereof, comprising:
   (i) at least one tRNA having bound thereto a non-proteinogenic amino acid having in its side-chain a charged group masked by a protecting group; and
   (ii)(a) a nucleic acid that encodes the peptide and contains at least one codon corresponding to an anticodon of the tRNA, or (b) a nucleic acid library that encodes the peptide library, each nucleic acid containing at least one codon corresponding to an anticodon of the tRNA;
   wherein the charged group is a carboxyl group and the combination of the charged group and the protecting group is an alkyl ester group or an aralkyl ester group.

3. A method of producing a charged non-proteinogenic amino acid-containing peptide or a peptide library thereof, comprising:
   a step of expressing a peptide or a peptide library in the translation system according to claim 1 and
   a step of removing the protecting group of a non-proteinogenic amino acid residue contained in the peptide or the peptides of the peptide library.

4. A method of producing a charged non-proteinogenic amino acid-containing or a peptide library thereof, comprising:
   a step of expressing a peptide or a peptide library in the cell-free translation system according to claim 2 and
   a step of removing the protecting group of a non-proteinogenic amino acid residue contained in the peptide or the peptides of the peptide library.

5. The cell-free translation system according to claim 1, further comprising a cell extract.

6. The cell-free translation system according to claim 2, further comprising a cell extract.

* * * * *

SEQUENCE LISTING

```
<160> NUMBER OF SEQ ID NOS: 11

<210> SEQ ID NO 1
<211> LENGTH: 37
<212> TYPE: DNA
<213> ORGANISM: Artificial
<220> FEATURE:
<223> OTHER INFORMATION: Synthesized primer T7pEpsSD6MY3.F37.

<400> SEQUENCE: 1
ggttaacttt aacaaggaga aaaacatgta ctactac                                37

<210> SEQ ID NO 2
<211> LENGTH: 39
<212> TYPE: DNA
<213> ORGANISM: Artificial
<220> FEATURE:
<223> OTHER INFORMATION: Synthesized primer eSD6MY3HFlag.R40

<400> SEQUENCE: 2
gtcgtcgtcc ttgtagtcgt ggtagtagta catgttttt                              39

<210> SEQ ID NO 3
<211> LENGTH: 40
<212> TYPE: DNA
<213> ORGANISM: Artificial
<220> FEATURE:
<223> OTHER INFORMATION: Synthesized primer T7pEpsSD6.F40.

<400> SEQUENCE: 3
ggcgtaatac gactcactat agggttaact ttaacaagga                             40

<210> SEQ ID NO 4
<211> LENGTH: 33
<212> TYPE: DNA
<213> ORGANISM: Artificial
<220> FEATURE:
<223> OTHER INFORMATION: Synthesized primer Flaguaa.R33.

<400> SEQUENCE: 4
cgaagcttac ttgtcgtcgt cgtccttgta gtc                                    33
```

<210> SEQ ID NO 5
<211> LENGTH: 39
<212> TYPE: DNA
<213> ORGANISM: Artificial
<220> FEATURE:
<223> OTHER INFORMATION: Synthesized primer eSD6MY3H2RY3.R40.

<400> SEQUENCE: 5
ttagtagtag tacctgtggt ggtagtagta catgttttt                     39

<210> SEQ ID NO 6
<211> LENGTH: 18
<212> TYPE: DNA
<213> ORGANISM: Artificial
<220> FEATURE:
<223> OTHER INFORMATION: Synthesized primer RY3uaa2.R18.

<400> SEQUENCE: 6
ttattagtag tagtacct                                             18

<210> SEQ ID NO 7
<211> LENGTH: 40
<212> TYPE: DNA
<213> ORGANISM: Artificial
<220> FEATURE:
<223> OTHER INFORMATION: Synthesized primer SD8M2-Y3H-G5S-4.F40.

<400> SEQUENCE: 7
aggtgatatt tatgtactac taccatggtg gaggaggagg                     40

<210> SEQ ID NO 8
<211> LENGTH: 41
<212> TYPE: DNA
<213> ORGANISM: Artificial
<220> FEATURE:
<223> OTHER INFORMATION: Synthesized primer G5S-4.an21.R41.

<400> SEQUENCE: 8
cccgcctccc gcccccccgtc ctagctacct cctcctccac c                  41

<210> SEQ ID NO 9
<211> LENGTH: 44
<212> TYPE: DNA
<213> ORGANISM: Artificial
<220> FEATURE:
<223> OTHER INFORMATION: Synthesized primer T7SD8M2.F44.

<400> SEQUENCE: 9
atactaatac gactcactat aggattaagg aggtgatatt tatg                44

<210> SEQ ID NO 10
<211> LENGTH: 20
<212> TYPE: DNA
<213> ORGANISM: Artificial
<220> FEATURE:
<223> OTHER INFORMATION: Synthesized primer G5S-4.R20.

<400> SEQUENCE: 10
tagctacctc ctcctccacc                                           20

<210> SEQ ID NO 11
<211> LENGTH: 21
<212> TYPE: DNA
<213> ORGANISM: Artificial
<220> FEATURE:
<223> OTHER INFORMATION: Synthesized Puromycin-DNA linker.
<220> FEATURE:

```
<221> NAME/KEY: misc_feature
<222> LOCATION: (21)..(21)
<223> OTHER INFORMATION: (SPC18)5-CC-Puromycin is bound to C. SPC18
      stands for 18-O-Dimet hoxytritylhexaethyleneglycol,
      1-[(2-cyanoethyl)-(N,N-diisopropyl)]-phosphoramidite.

<400> SEQUENCE: 11
cccgcctccc gcccccgtc c                                              21
```